US008883441B2

(12) United States Patent
Vedrine et al.

(10) Patent No.: US 8,883,441 B2
(45) Date of Patent: Nov. 11, 2014

(54) METHOD FOR DETECTING AND COUNTING MICRO-ORGANISMS IN A SAMPLE

(75) Inventors: Bruno Vedrine, Pontgibaud (FR); Aline Lachaise, Rilhac-Rancon (FR); Vincent Carre, Jabreilles-les Bordes (FR)

(73) Assignee: Metis Biotechnologies, Limogenes (FR)

( * ) Notice: Subject to any disclaimer, the term of this patent is extended or adjusted under 35 U.S.C. 154(b) by 1214 days.

(21) Appl. No.: 10/529,654

(22) PCT Filed: Oct. 1, 2003

(86) PCT No.: PCT/FR03/02873
§ 371 (c)(1),
(2), (4) Date: May 31, 2005

(87) PCT Pub. No.: WO2004/031403
PCT Pub. Date: Apr. 15, 2004

(65) Prior Publication Data
US 2005/0202518 A1  Sep. 15, 2005

(30) Foreign Application Priority Data
Oct. 1, 2002  (FR) .................... 02 12119

(51) Int. Cl.
C12Q 1/04 (2006.01)
G01N 33/53 (2006.01)
C12Q 1/02 (2006.01)
C12Q 1/24 (2006.01)
C12N 11/00 (2006.01)
C12N 11/16 (2006.01)
C12N 11/02 (2006.01)

(52) U.S. Cl.
USPC ................. 435/34; 435/7.1; 435/7.2; 435/29; 435/30; 435/174; 435/176; 435/177; 435/180

(58) Field of Classification Search
None
See application file for complete search history.

(56) References Cited

U.S. PATENT DOCUMENTS

| 3,704,204 | A | * | 11/1972 | Heck .............................. 435/38 |
| 5,429,927 | A |   | 7/1995  | Afseth et al. |
| 5,510,243 | A | * | 4/1996  | Boyd et al. ..................... 435/18 |
| 5,534,415 | A |   | 7/1996  | Orenga |
| 5,620,865 | A | * | 4/1997  | Chen et al. ..................... 435/34 |
| 5,843,699 | A | * | 12/1998 | Strenkoski et al. ............. 435/34 |
| 5,861,270 | A |   | 1/1999  | Nelis |
| 6,120,987 | A |   | 9/2000  | Aspe |

FOREIGN PATENT DOCUMENTS

| DE | 1 554 193 | 10/1979 |
| EP | 0 333 560 | 9/1989 |
| EP | 0 877 092 A1 | 11/1998 |
| EP | 1 546 366 | 6/2009 |
| GB | 1554193 A | 10/1979 |
| JP | 08-275773 | 10/1996 |
| JP | 10-509031 | 9/1998 |
| JP | 10-313892 | 12/1998 |
| WO | 89/04372 | 5/1989 |
| WO | WO 89/08714 | 9/1989 |
| WO | 95/31481 | 11/1995 |
| WO | WO 96/14432 | 5/1996 |
| WO | 99/02650 A1 | 1/1999 |
| WO | WO 2004/031403 A1 | 4/2004 |

OTHER PUBLICATIONS

Technical Bulletin for Fraser *Listeria* Enrichment Broth Base: for the selective enrichment of *Listeria* in the 2-step method acc. to D.G.AL. and ISO 11290-1 (1996). EMD Merck KGaA, Damstadt, Germany, 2002. http://www.emdchemicals.com/analytics/Micro_Manual/TEDISdata/prods/1_10398_0500.html. Retrieved, Mar. 9, 2009.*
Kaclikova et al. Journal of Microbiological Methods, vol. 46 Issue 1 Jul. 2001, p. 63-67.*
Olsen et al. Plant and Soil 186:75-79, 1996.*
Patel et al. (Journal of Food Protection, 1995 vol. 58, No. 3, p. 244-250).*
Ray, Bibek (Injured Index and Pathogenic Bacteria. 1989. CRC Press Inc. Boca Raton, Florida. p. 78).*
Sigma catalog 1996 p. 2179-2181.*
Rompre et al. Journal of Microbiological Methods 49 ( Mar. 2002) 31-54.*
J. Stan Bailey et al., "Universal Preenrichment Broth for the Simultaneous Detection of *Salmonella* and *Listeria* in Foods", Journal of Food Protection, Apr. 1992, pp. 256-259, vol. 55, No. 4.
Stephen C. Edberg et al., "Rapid Spot Test for the Determination of Esculin Hydrolysis", Journal of Clinical Microbiology, Aug. 1976, pp. 180-184, vol. 4, No. 2.
Dynabeads Protein A—Package Insert dated Aug. 14, 2001.
Calabrese J.P. and Bissonnette G.K., "Improved membrane filtration method incorporating catalase and sodium pyruvate for detection of chlorine-stressed coliform bacteria", *Applied and Environmental Microbiology*, Nov. 1990, p. 3558-3564.
Brailsford M.A. and Gatley S., "Industrial application of flow cytometry for the rapid detection of microorganisms", *New Technique in Food and Beverage Microbiology*, 1993, p. 87-100.
Kayser A. and Van Der Ploeg G., "Growth inhibition of staphylococci by sodium thiosulphate", *J. Appl. Bact.* 28(2), 1965, p. 285-293.
McDonald L.C. et al., "Enhanced recovery of injured *Escherichia coli* by compounds that degrade hydrogen peroxide of block its formation", *Applied and Environmental Microbiology*, Feb. 1983, p. 360-365.
Nexmann Jacobsen C. et al., "Viability staining and flow cytometric detection of *Listeria monocytogenes*", *Journal of Microbiological Methods*, 1997, p. 35-43.

(Continued)

*Primary Examiner* — Oluwatosin Ogunbiyi
(74) *Attorney, Agent, or Firm* — Arent Fox LLP

(57) ABSTRACT

A method for detecting and counting the microorganisms in a sample is described. The method comprises:
a) selectively enriching the microorganism sought in the sample,
b) inducing or activating at least one enzymatic activity of the microorganism,
c) immunomagnetically concentrating the microorganism,
d) fluorescently labeling the microorganism, and
e) detecting and analyzing the fluorescence making possible the numeration or counting of the microorganisms sought by flow cytometry, filtration cytometry or fluorescence microscopy.

16 Claims, No Drawings

(56) References Cited

OTHER PUBLICATIONS

Silvestri A-C. et al., "Extraction of *Enterobacteriaceae* from foods by immunomagnetic separation before flow cytometric detection", *Sciences des Aliments*, 1997, p. 361-370.

Van Poucke S.O. and Nells H.J., "A 210-min solid phase cytometry test for the enumeration of *Escherichia coli* in drinking water", *Journal of Applied Microbiology*, 2000, p. 390-396.

English Translation of the Letters in Opposition and the Appeal Proceeding against EPO, Jul. 8, 2011.

Alvarez-Barrientos, Alberto et al., "Applications of Flow Cytometry to Clinical Microbiology"; Clinical Microbiology Reviews, Apr. 2000, p. 167-195.

Amann, R.I., "Fluorescently labelled, rRNA-targeted oligonucleotide probes in the study of microbial ecology"; Molecular Ecology 1995, vol. 4, pp. 543-554.

Barer, Michael R., et al., "Bacterial Viability and Culturability"; Advances in Microbial Physiology, vol. 41, 1999, pp. 93-137.

Birk, Ruth et al., "Synthesis of Isopropyl-1-Thio-β-$_D$-Glucopyranoside (IPTGlc), an Inducer of *Aspergillus niger* B1 β-Glucosidase Production"; Applied Biochemistry and Biotechnology; vol. 66, 1997, pp. 25-30; Humana Press, Inc.

Breeuwer, Peter et al., "Characterization of Uptake and Hydrolysis of Fluorescein Diacetate and Carboxyfluorescein Diacetate by Intracellular Esterases in *Saccharomyces cerevisiae*, Which Result in Accumulation of Fluorescent Product"; Applied and Environmental Microbiology; Apr. 1995; vol. 61, No. 4, pp. 1614-1619.

Cocito, Carlo et al., "Paratuberculosis"; Clinical Microbiology Reviews; Jul. 1994; vol. 7, No. 3; pp. 328-345.

Dassy, B., et al., "Production of type 5 capsular polysaccharide by *Staphylococcus aureus* grown in a semi-synthetic medium"; Journal of General Microbiology (1991); vol. 137; pp. 1155-1162.

Davey, Hazel M., et al., "Flow Cytometry and Cell Sorting of Heterogeneous Microbial Populations: the Importance of Single-Cell Analyses"; Microbiological Reviews; Dec. 1996; vol. 60, No. 4; pp. 641-696.

Dudley, Richard F., "The Ciba Corning ACS: 180™ Automated Immunoassay System", vol. 14, No. 2, Summer 1991.

Garcia-Armesto, M.R., et al., "Modern microbiological methods for foods: Colony count and direct count methods. A review"; Microbiologia Sem, vol. 9 (1993), pp. 1-13.

Grant, Irene R., et al., "Isolation of *Mycobacterium paratuberculosis* from Milk by Immunomagnetic Separation"; Applied and Environmental Microbiology, vol. 64, No. 9; Sep. 1998; pp. 3153-3158.

Gregori, Gerald et al., "Resolution of Viable and Membrane-Compromised Bacteria in Freshwater and Marine Waters Based on Analytical Flow Cytometry and Nucleic Acid Double Staining"; Applied and Environmental Microbiology; vol. 67, No. 10, Oct. 2001; pp. 4662-4670.

Haugland, Richard P., "Detecting Enzymatic Activity in Cells Using Fluoregenic Substrates"; Biotechnic & Histochemistry, vol. 70, No. 5,; 1995; pp. 243-251.

House, Deborah, et al., "Typhoid fever: pathogenesis and disease"; Current Opinion in Infectious Diseases 2001; 14:573-578.

Humbert, F., et al., "Rapid identification of *Salmonella* from poultry meat products by using 'Mucap test'"; International Journal of Food Microbiology; 8 (1989); 79-83; Elsevier Science Publishers B.V.

Iannelli, Domenico, et al., "Simultaneous Identification of Antibodies to *Brucella abortus* and *Staphylococcus aureus* in Milk Samples by Flow Cytometry"; Journal of Clinical Microbiology; vol. 36, No. 3, Mar. 1998; pp. 802-806.

Kramer, Pamela A. et al., "Media Selective for *Listeria monocytogenes*"; J. Appl. Bact.; vol. 32, pp. 381-394, 1969.

Lopez-Amoros, R., et al., "Flow Cytometric Assessment of *Escherichia coli* and *Salmonella typhimurium* Starvation-Survival in Seawater Using Rhodamine 123, Propidium Iodide, and Oxonol"; Applied and Environmental Microbiology; vol. 61, No. 7; Jul. 1995; pp. 2521-2526.

Manafi, M., "New developments in chromogenic and fluorogenic culture media"; International Journal of Food Microbiology; vol. 60; 2000; pp. 205-218.

Mason, D.J., et al., "The ability of membrane potential dyes and calcafluor white to distinguish between viable and non-viable bacteria"; Journal of Applied Bacteriology 1995; vol. 78; pp. 309-315.

McClelland, R.G. et al., "Detection of *Salmonella typhimurium* in Dairy Products with Flow Cytometry and Monoclonal Antibodies"; Applied and Environmental Microbiology; vol. 60, No. 12; Dec. 1994; pp. 4255-4262.

Moter, Annette, et al., "Fluorescence in situ hybridization (FISH) for direct visualization of microorganisms"; Journal of Microbiological Methods, vol. 41, 2000; pp. 85-112.

Nebe-Von Caron; G., et al., "Viability assessment of bacteria in mixed populations using flow cytometry"; Journal of Microscopy; vol. 179, Pt. 1; Jul. 1995; pp. 55-66.

Nedergaard, N., et al., "Dicarboxy-Dichlorofluorescein: A New Fluorescent Probe for Measuring Acidic Intracellular pH"; Analytical Biochemistry; vol. 187; 1990; pp. 109-114.

Notermans, Serve H.W., et al., "Phosphatidylinositol-Specific Phospholipase C Activity as a Marker to Distinguish between Pathogenic and Nonpathogenic *Listeria* Species"; Applied and Environmental Microbiology; vol. 57, No. 9; Sep. 1991; pp. 2666-2670.

Olsson, Margaretha, et al., "Identification of *Salmonellae* with the 4-Methylumbelliferyl Caprilate Fluorescence Test" ; Journal of Clinical Microbiology; vol. 29, No. 11; Nov. 1991; pp. 2631-2632.

Ouyang, Shu et al., "Promoter Analysis of the *cap8* Operon, Involved in Type 8 Capsular Polysaccharide Production in *Staphylococcus aureus*"; Journal of Bacteriology; vol. 181, No. 8; Apr. 1999; pp. 2492-2500.

Perez-Pons, Josep A., et al., "Induction and preliminary characterization of intracellular β-glucosidases form a cellulolytic *Streptomyces* strain"; FEMS Microbiology Letters 128 (1995); pp. 235-239.

Pinder, A.C. et al., "Rapid assay for pathogenic *Salmonella* organisms by immunofluorescence flow cytometry"; Journal of Microscopy; vol. 176, Pt. 1; Oct. 1994; pp. 17-22.

Robinson, J. Paul, "Overview of Flow Cytometry and Microbiology"; Current Protocols in Cytometry; 2004; 11.1.1-11.1.4; John Wiley and Sons, Inc.

Salzman, Gary C., et al., "Rapid Identification of Microorganisms by Circular-Intensity Differential Scattering"; Applied and Environmental Microbiology; vol. 44, No. 5; Nov. 1982; pp. 1081-1085.

Seo, K. H., et al., "Immunomagnetic Separation and Flow Cytometry for Rapid Detection of *Escherichia coil* O157:H7"; Journal of Food Protection; vol. 61, No. 7; 1998; pp. 812-816.

Sheagren, John N., Medical Progress: *Staphylococcus aureus*, The Persistent Pathogen (First of Two Parts); The New England Journal of Medicine; May 24, 1984.

Sheagren, John N., Medical Progress: *Staphylococcus aureus*, The Persistent Pathogen (Second of Two Parts); The New England Journal of Medicine; vol. 310, No. 22; 1984.

Skjerve, Eystein, et al., "Detection of *Listeria monocytogenes* in Foods by Immunomagnetic Separation"; Applied and Environmental Microbiology; vol. 56, No. 11; Nov. 1990; pp. 3478-3481.

Skjerve, Eystein, et al., "Immunomagnetic separation of Salmonella from foods"; International Journal of Food Microbiology; 14 (1991); pp. 11-18.

Sompolinsky, David et al., "Encapsulation and Capsular Types in Isolates of *Staphylococcus aureus* from Different Sources and Relationship to Phage Types"; Journal of Clinical Microbiology; vol. 22, No. 5; Nov. 1985; pp. 828-834.

Soro, O., et al., "Phosphatase Activity of Staphylococci Is Constitutive in Some Species and Repressed by Phosphates in Others"; Journal of Clinical Microbiology; vol. 28, No. 12; Dec. 1990; pp. 2707-2710.

Steen, Harald B., "Simultaneous Separate Detection of Low Angle and Large Angle Light Scattering in an Arc Lamp-Based Flow Cytometer"; CYTOMETRY 7: 445-449 (1986), Alan R. Liss, Inc.

Tomoyasu, Takahiro, "Improvement of the Immunomagnetic Separation Method Selective for *Escherichia coli* O157 Strains"; Applied and Environmental Microbiology; vol. 64, No. 1; Jan. 1998; pp. 376-382.

(56) References Cited

OTHER PUBLICATIONS

Tortorello, Mary Lou, et al., "Antibody-Direct Epifluorescent Filter Technique for Rapid, Direct Enumeration of *Escherichia coli* O157:H7 in Beef"; Applied and Environmental Microbiology; vol. 60, No. 10; Oct. 1994; pp. 3553-3559.

Tortorello, Mary Lou et al., "Quantitative analysis and isolation of *Escherichia coli* O157:H7 in a food matrix using flow cytometry and cell sorting"; FEMS Immunology and Medical Microbiology 19 (1998); pp. 267-274.

Venturi, Leandra Lorice, et al., "Extracellular β-$_D$-glucosidase from *Chaetomium thermophilum* var. *coprophilum* : production, purification and some biochemical properties"; J. Basic Microbiol.; vol. 42 (2002); pp. 55-66.

Vlieger, A.M., et al., "Quantitation of Polymerase Chain Reaction Products by Hybridization-Based Assays with Fluorescent, Colorimetric, or Chemiluminescent Detection"; Analytical Biochemistry; vol. 205; (1992); pp. 1-7.

Wallner, Guenter, et al., "Flow Cytometric Analysis of Activated Sludge with rRNA-Targeted Probes"; Applied and Environmental Microbiology; vol. 61, No. 5; May 1995; pp. 1859-1866.

Yang, Ling et al., "A Sennoside-Hydrolizing β-Glucosidase from *Bifidobacterium* Sp. Strain SEN Is Inducible"; Biol. Pharm. Bull.; vol. 19(5); (1996); pp. 701-704.

PCT/FR03/02873 International Search Report dated Mar. 4, 2004.

\* cited by examiner

METHOD FOR DETECTING AND COUNTING MICRO-ORGANISMS IN A SAMPLE

This application is a 371 of PCT/FR2003/02873, filed Oct. 1, 2003, which claims priority to French Patent Application No. 02/12119, filed Oct. 1, 2002. The entire contents of each of the above applications is herein incorporated by reference.

The present invention relates to a method for detecting and counting microorganisms in a sample as well as in an enrichment medium that is selective for the microorganism sought.

The present invention applies to the detection of microorganisms such as *Listeria monocytogenes, Salmonella, Staphylococcus aureus, Escherichia coli, Mycobacterium avium paratuberculosis*, and *Legionella pneumophila*. This detection is carried out preferably by flow cytometry of samples of any number of types, such as samples of food, solids, liquids, plants, animals, etc., as well as tissue samples from animals and, in particular, humans.

Microbial contamination is a major concern to the food processing industry because contamination can cause serious product degradation and delay the delivery of stocks that await required quality analyses. The expected criteria for microbiological analyses concern two areas. First, the contamination state must be monitored as precisely as possible, thus requiring highly sensitive and discriminative analysis methods. Second, these methods must be rapid so that production batches can be scheduled for release, and they must make predictive microbiological analyses possible.

The rapidity criterion is decisive if marketing a product at risk of contamination is to be avoided. Classical analysis techniques always necessitate incubation steps that are lengthy with respect to the requirements for efficient food processing. Moreover, the classical analyses do not take into account bacteria that have lost their ability to multiply, even though such bacteria conserve metabolic activity capable of reactivating if exposed to a particular condition such as an increase in temperature should refrigeration be insufficient at some point in the food chain or when passing through the customer's organism.

Furthermore, in the environment, the rapidity and sensitivity of microbiological analysis methods applied to technical or drinking water are the decisive criteria, as these water sources can contaminate people directly (in the case of drinking water) or indirectly through environmental pollution (such as *Legionella* in air-conditioning systems or the contamination of surfaces that come into contact with food).

Among the classical microbiological techniques for detecting and counting microorganisms, Petri dish culturing is widely used.

The Petri dish counting method is the conventional means by which microbial populations are estimated. Growth and division are the foundations of this microbiological analysis method for searching for viable bacteria. In this case, cultivability is associated with viability. Cultivability, in fact, is defined as the capacity of a single cell to give rise to an observable or visible population on the surface of a culture dish.

This technique has been used for decades and has shown itself to be effective for the protection of human health at a relatively low cost. In recent years, a number of innovations have been introduced regarding culture media (chromogenic media), automation of culture media preparation, dilution of ground samples in media, and spreading and counting colonies on Petri dishes (Garcia-Armesto et al., 1993). However, the classical techniques remain weak in two respects. First, they are not very sensitive due to their fundamental requirement that the bacteria be grown on culture media in Petri dishes, the aforementioned culture media being variably effective for the selective growth of germs according to the food product tested. Second, culturing in Petri dishes requires that the germs sought be in physiologically optimal conditions to be able to grow in a selective culture medium. Yet, quite often the bacteria initially present in a sample cannot be detected later by classical microbiological techniques, namely by culturing in standard media. This can be explained in two ways: either the bacteria are dead as a result of extreme stress (thermal or osmotic shock, a lack of nutrients, etc.) or they lost their capacity to proliferate in standard culture media and are thus considered as viable but non-cultivable bacteria (Barer et al., 1999). It is therefore important to be able to detect these bacteria in a sample.

Recently it has been shown that several cultivable species of bacteria, when they are subjected to a lack of nutrients or to another physical stress (thermal, hydric, etc.), can enter into a state of cellular survival during which they are not detectable by cultivability tests (for example by Petri dish culturing).

This is why DNA amplification techniques, which offer greater specificity in relation to the microorganisms being sought and which are automatable, were developed. These techniques consist of the detection of a microorganism's specific nucleotide sequences (after genic amplification). This approach however still does not make it possible to count microorganisms in a sample.

In terms of specificity, genetic probes (DNA, RNA, PNA, molecular beacons, etc.) are an alternative to the use of fluorescent antibodies. These probes must be labeled using a fluorochrome and hybridized to the cells under study without the latter having to be lysed beforehand: this is in situ hybridization. In this case, the probes used target 16S or 23S PARN, which makes it possible both to assure the detection's specificity and to increase the signal linked to the number of copies of this cellular RNA (Moter et al., 2000).

Other techniques, such as immunological methods (including ELISA), consist of detecting the antibodies for microbial antigens by luminescence or fluorescence. Even if these methods are easily automatable and sensitive, they provide limited information because they do not make it possible to count the microorganisms present. Moreover, these methods are occasionally criticized with regard to their specificity as the antibodies used can present restricted microbial antigen recognition spectra (Tortorello et al., 1994).

Whichever methods are employed, they all require that the bacteria sought undergo an enrichment phase in order to achieve acceptable sensitivity and specificity.

Cytometric analyses, of which flow cytometry is an example, present the advantage of allowing the direct detection of germs that are labeled in advance with a fluorescent molecule. Moreover, this labeling can suggest the viability of the bacteria. Detection using a flow cytometer is direct, quantitative, and only takes a few minutes.

Flow cytometry, by its successful adaptation to biology and medicine, is well positioned to be adapted for high-throughput microbiological analysis (Alvarez-Barrientos et al., 2000; Davey et al., 1996). One of the technical features of flow cytometry is that it can make possible, in less that 24 or 48 hours, analyses of populations defined by particular growth characteristics (fecal coliform at 44° C., psychrophilic flora), which after enrichment in a selective broth can be detected directly by flow cytometry, rather than waiting for growth on a specific medium.

In the last few years, a number of commercial cytometers have been developed for the analysis of eukaryotic cells but which are not appropriate for the detection of microorganisms. However, developments in photomultipliers, the introduction of lasers, and optical system improvements (focusing, quartz analysis cells) make it possible for the majority of cytometers today to quantify bacteria and viruses (Salzman et al., 1982, Steen et al., 1986). The most significant progress involved the ability to measure the size of the eukaryotic or prokaryotic cells analyzed, first by a photodiode then by a photomultiplier. Thus, it is now possible to select a cellular population of defined size (microorganisms for example) for an analysis of its emitted fluorescence. The window of analysis thus created makes it possible to concentrate the cytometer's analytical power on predefined events, which in turn makes it possible to obtain reliable differentiation between the fluorescence signal emitted by the microorganism and the background noise of the matrix.

The fluorescent labels used label microbial populations universally and have a broad action spectrum. These include DNA intercalators as well as markers for bacterial membrane potentials or respiratory activity (Lopez-Amoros et al., 1995; Grepori et al., 2001). Measurement of the size and granulosity of intracellular contents can be associated with fluorescence signals. The use of fluorescent molecules to detect viable microorganisms by flow cytometry is well known at present (Davey et al., 1996; Nebe-von Caron et al., 1995). The principle is to detect an enzymatic activity present in all the microorganisms. In all cases these activities are very broad spectrum and essential to cell survival. Of the multiple examples described in the literature, the most relevant involve substrates that reveal esterase activity in its totality, such as fluorescein diacetate (FDA) or its homologue carboxyfluorescein diacetate (CFDA) (Breeuwer et al., 1995).

Drocourt et al. (FR 2 764 305) describe a method for labeling (FDA and CDFA) all the viable microorganisms in a complex sample based on the detection of esterase activity and deletion in particular, using a counterstain for the sample's autofluorescence.

Breeuwer et al. (WO05/00660) describe a method for measuring the viability of microorganisms in a sample by using fluorescent labels. The method consists of measuring the time required for half of the fluorescence emitted by these microorganisms to be lost.

Inoue et al. (EP 1 203 825) use polymethine to indicate nitrite ion reduction activity in microorganisms. This is an a priori cell activity that is detectable in all bacteria.

Rocco et al. (WO00/34509) use antibiotics onto which fluorescent molecules are conjugated to indicate microorganisms.

Fazzi et al. (WO00/067065) have developed a method that makes it possible to differentiate bacteria by their Gram stains, by using a mixture of acridine orange and fluorescein. The detection of labeled microbial populations is accomplished by flow cytometry Jespersen et al. (WO02/00036) also have developed a Gram-staining method based of the use of molecules that recognize the structural differences between Gram-positive bacteria (glycan structures on the cell surface) and Gram-negative bacteria (presence of lipopolysaccharide). However, this method does not make it possible to measure bacterial viability.

Pyle et al. (WO95/31481) use CTC as an indicator molecule for microorganism respiratory activity. This detection is coupled with immunomagnetic enrichment and/or immunological detection using fluorescein-labeled antibodies.

However, the fluorescent labels that indicate viability cited above have too broad a spectrum to provide the specificity necessary to detect specific microorganisms The combination of molecular biology techniques (using fluorescence-labeled nucleotide probes) and flow cytometry is a rather recent approach (Amann et al., 1995; Wallner et al., 1995).

However, even though this approach is suitable for Gram-negative microorganisms work still must be done in order to label Gram-positive bacteria specifically. Vlieger et al., (1992), describe the use of flow cytometry to detect nucleic acids amplified by PCR by hybridizing the aforementioned fragments to beads.

Notably, flow cytometry has been used to enumerate total bacteria or yeast in milk, as well as in preparations containing meat, fermented milk, frozen vegetables, or raw milk. For these, viability markers were used (Breeuwer et al., 1995). Morphological criteria for size and structure, which can be analyzed by flow cytometry, were added to this first selection criterion.

Detection of microorganisms (genus and species) more specifically in food concerns, in particular, pathogenic flora such as *Salmonella, Listeria monocytogenes, Escherichia coli* 0157:H7, *Staphylococcus aureus*, and *Brucella abortus* (McClelland et al., 1994; Iannelli et al., 1998; Pinder et al., 1994; Skjerve et al., 1990, 1991; Tomayasu et al., 1998; Tortorello et al., 1998).

The most common fluorescent labels used to identify bacterial genera remain antibodies, for which protocols are numerous and varied, but which are not very sensitive if used directly on food products. In effect, the numeration of a small number of cellular events in a food sample is difficult because of the presence of a high level of background noise in the matrix and endogenous flora and because choosing an appropriate fluorescent label to obtain accurate cell viability data is not trivial. Thus, it is recommended to use multiple fluorescent labels (antibodies, stoichiometric probes, DNA intercalators, enzymatic substrates, etc.) to discriminate between fluorescent bacteria and particles between different bacterial species.

To improve the detection of bacterial genera and species, immunomagnetic separation has been used with success to separate pathogenic microorganisms in a complex food matrix. Two companies, Dynal (Oslo, Norway) and Vicam (Watertown, USA), market magnetic beads onto which antibodies that recognize pathogenic bacteria are conjugated. However, conventional applications still require spreading on a Petri dish after incubation with a selective enrichment medium, and at times confirmation tests, a need which arises essentially because of the lack of selectivity of antibodies used or of non-specific interactions of the natural flora with the magnetic beads' support (Tomayasu et al., 1998). For example, it is recognized that strains of *Vibrio parahaemolyticus* can adsorb to the surface of magnetic beads non-specifically and that this adsorption capacity depends on the *Vibrio* strain's identity. Structural improvement to these paramagnetic beads involves encapsulating the bead in a chemical structure that is less reactive with the medium (encapsulated nanobeads, Estapor).

Immunomagnetic separation has been shown effective in recovering eukaryotic cells from liquids and in isolating microorganisms from samples as varied as food, milk, and feces (Grant et al., 1998; Skjerve et al., 1990, 1991, Pinder et al., 1994; Seo et al., 1998). Paramagnetic beads that present on their surface antibodies directed against membrane surface antigens are commercially available. They make it possible to concentrate bacteria in a complex sample and improve the sensitivity of subsequent techniques such as PCR, nucleic probe hybridization, immunofluorescence, and flow cytometry. This immunoconcentration, which is performed by isolating bacteria-bead conjugates on a tube wall, makes it possible to eliminate inhibiting agents present in the sample simultaneously. Moreover, it constitutes a selection phase.

The use of immunofluorescence in conjunction with flow cytometry responds well to this specificity problem. Immunological properties of pathogenic bacteria in food have been known for some time and are widely used in rapid-detection tests. These specific FITC-labeled antibodies have been used to mark *Salmonella* added to samples of milk and eggs and in the rinse water from contaminated chicken carcasses (McClelland et al., 1994). Using immunofluorescence and flow cytometry in tandem has also been applied to the detection of *Escherichia coli* O157:H7 in samples of meat artificially contaminated after destruction of the meat's natural flora (Seo et al., 1998).

However, in all these cases, pretreatment (chemical or immunoseparation) of the sample is required before analysis and the detection threshold does not drop below 10 000 cells per gram of product, which is too high with respect the requirements for detecting pathogenic bacteria in food.

Forrest et al., 1979, (U.S. Pat. No. 4,141,687) and Ithakissios et al., 1978, (U.S. Pat. No. 4,115,534) describe the synthesis of magnetic particles which when conjugated to recognition molecules make it possible to extract eukaryotic and prokaryotic cells from a complex mixture by using a magnetic field.

Coulter Electronics (UK 1,561,042) describes the use of flow cytometry to isolate and analyze particles and cells linked to these particles.

Pinder et al. (WO98/20214) have developed magnetic beads of a size less than 1 micron (100 nm being the preferred size) that are fluorescent The interest in such beads for use in extracting and marking microorganisms rests in their tininess. It is not necessary to detach the aforementioned beads from the microorganisms in order to detect the microorganisms using flow cytometry.

Pyle et al. (WO 95/31481) use magnetic beads to concentrate bacteria from a complex sample. These bacteria are then labeled green with a fluorescent antibody (fluorescein for example) and the cell's respiratory activity is detected by CTC (cyano tetrazolium chloride) which induces red fluorescence in the cells; detection is made using fluorescence microscopy.

Senyei et al. (EP/0016552) have conjugated protein A, which can be linked to a number of antibodies, to magnetic beads in order then to recover the cells that have an antibody linked to their surface.

Vesey et al. (WO96/31777) use flow cytometry to analyze the complexes formed by latex beads attached to microorganisms via a fluorescent antibody intermediate. They describe the use of a fluorescent antibody to label microorganisms that have been immunomagnetically extracted from a sample.

Fortin et al. (WO99/47933) use latex beads ranging between 0.08 and 0.5 micron in size to which cell recognition antibodies are conjugated. Complexes observable by flow cytometry are thus formed, according to size and structure characteristics.

The detection of microorganisms in a sample can also be performed by the detection of specific enzymatic activities or by the use of chromogenic or fluorescent substrates. Manafi's (2000) review is a rather complete update of the strategies used to identify microorganisms based on the presence or lack of particular enzymatic activities in the microorganism. The principle dichotomous keys are the demonstration of particular activities by esterases (which only hydrolyze fatty acids with defined aliphatic chain lengths), glycosides (hydrolysis of various sugars), phosphatases, and sulfatases. The substrates used are comprised of one target part, which is recognized by the enzyme sought, and a label part. When this label part is linked to the target, it only emits a visible signal (chromogenic or fluorescent) after hydrolysis of the target-label linkage. The most widely used indication methods for these metabolic activities involve adding these substrates to culture media. The substrates, when assimilated by the microorganisms inside a colony, give the colony a distinctive color. The combination of selective media and substrates (one or several per medium) makes it possible to obtain a precise identification of the microorganism sought by observing the form and color of the bacteria.

Thus, so that a colony is colored on a chromogenic medium, the substrate must be expelled outside of the microorganism, inside the colony.

Schabert et al. (WO99/48899) describe a synthetic pathway for a fluorescent substrate (under UV excitation) which makes it possible to indicate specific phosphatyl-inositol activity by phospholipase C. This substrate (which has 4-methylumbelliferone as its fluorescent molecule) is used in the design of two culture media that make possible the identification of *Listeria monocytogenes* and *Bacillus cereus*. This substrate is not, however, specific enough for a bacterial genus to be used in the context of the present invention.

Conrad et al. (WO00/03034) developed fluorescent substrates with esculin as the fluorescent molecule. The detection methods and precise use of these substrates to identify microorganisms are not described.

Berg et al. (U.S. Pat. No. 5,292,644) describe the use of 4-methylumbelliferone-β-D-galactosidase, which is excitable by UV light ($\lambda_{exc}$=365 nm), for detecting galactosidase activity in bacteria regardless of whether these microorganisms are grown in liquid or solid media. The detection is made by exciting the methylumbelliferone with UV light after it has been precipitated from the external media.

Nelis et al. (WO 98/13515) describe the use of chromogenic or fluorescent substrates following UV excitation, which makes it possible to demonstrate beta-D-galactosidase or beta-D-glucuronidase activity in microorganisms. The described technique is limited to the detection of the aforementioned microorganisms when they are labeled on solid culture media or retained on a filter.

Rambach Alain (WO 00/53799) uses glucose and phosphate substrates conjugated with chromogenic molecules to detect *Staphylococcus aureus* in a specific medium containing deferoxamine. The detection is based on the observation of chromogenic compounds in the bacterial colony that have been expelled by the bacteria inside the colony. The identification of *Staphylococcus aureus* is based on the observation of chromogenic compounds resulting from the action of the enzymes phosphatase and glucosidase.

Cooke et al. (WO 00/41409) specifically label *Salmonella* using a chromogenic substrate specific to the octanoate-esterase (or caprylate-esterase) activity of the aforementioned microorganism. The use of caprylate-esterase as a means of *Salmonella* identification has been described for a number of years (Humbert et al., 1989) and shows little efficacy when used in conjunction with solid culture media. In the patent application by Cooke et al., a substrate that makes it possible to detect β-D-galactosidase is added to the medium in order to achieve greater specificity.

The present invention proposes to remedy the inconveniences of the prior art by providing a method for detecting and numerating or counting microorganisms in a solid or liquid sample under significantly improved time and specificity conditions.

Within the scope of the present invention, the search for microorganisms can be carried out from samples of food-processing origin, such as meat products, egg products, water, milk products including milks, fruit juices, crop products and their derivatives, as well as from samples of animal origin, including human origin, such as all types of tissues, feces, and blood.

The method of the invention comprises in particular three steps that are selective and specific to the microorganism sought in a sample, namely the selective enrichment of the microorganism in question, the activation of the aforementioned microorganism in a conditioning medium, and the fluorescent labeling of the aforementioned microorganism.

Indeed, the method for detecting and numerating or counting microorganisms in a sample according to the invention comprises five steps of which certain can be concomitant and for which the order can vary according to the microorganism sought.

The method of detection according to the invention comprises the steps of:
a) selectively enriching the microorganism sought in the sample,
b) conditioning the aforementioned microorganism,
c) immunomagnetically concentrating the conditioned microorganism,
d) fluorescent labeling of the concentrated microorganism, and
e) detecting and analyzing the fluorescence.

One of the objectives of the present invention is to overcome the lack of sensitivity and specificity in microorganism detection methods of the prior art. The method according to the invention makes it possible to obtain very low detection thresholds, on the order of from 10 to 100 microorganisms per gram of sample, which is to say thresholds 100 to 1 000 times lower that those of the prior art.

Another objective of the invention is to make possible microorganism detection in less than 24 hours, which in particular is achieved by an enrichment and conditioning step for the microorganism sought in less than 18 hours, fluorescent labeling in less than 3 hours, and detection by flow cytometry in a few minutes.

The first step of the method according to the invention is a selective enrichment step for the microorganism sought in the sample, this step having twin aims. This step not only makes possible the multiplication of the aforementioned microorganism but also the revivification of the aforementioned microorganism in the case where the aforementioned microorganism is stressed, for example. This enrichment step is carried out for a period of 8 to 15 hours in a composition comprising nutrients adapted for the growing of the microorganism sought. This composition also comprises agents that serve to destroy oxygen-reactive species as well as anti-oxidizing agents that can be present in the sample.

This composition is also intended to restore or preserve viability in a microorganism whose cultivability criterion is temporarily lost for whatever reason, for example following stress such as heat treatment.

The significance of such a step is then to be able to detect and count the microorganisms in question in order to include them in the analysis of the sample. This is important because such microorganisms are susceptible to later reactivation following a particular event such as a change in temperature, thus these microorganisms can become a danger to the consumer's health or can give rise to an underestimation of the level of contamination or infection of the aforementioned sample.

In a preferred embodiment of the invention, the composition used in the selective enrichment step for the microorganism sought in the sample comprises:
sodium pyruvate at a concentration ranging between 1 and 20 g/L, preferably between 1 and 10 g/L, and more preferably between 4 and 6 g/L,
sodium thiosulfate at a concentration ranging between 0.5 and 5 g/L, preferably between 0.5 et 3 g/L, and still more preferably approximately 2 g/L,
catalase at a concentration ranging between 500 and 20 000 u/L, preferably between 2 000 and 8 000 u/L, and still more preferably approximately 5 000 u/L.

In addition to the two aims proposed to be attained for the aforementioned composition, the destruction of the competitive flora of the microorganism sought can also be possible if such a step is included according to the sample or the aforementioned microorganism. Thus, the composition according to the invention can comprise in addition at least one antimicrobial agent.

By "antimicrobial" agent or "selective agent", it is meant all compounds capable of destroying or inhibiting the competitive flora of the microorganism sought. It should be stressed that the aforementioned antimicrobial or selective agent can be an antibiotic.

Of course, the antimicrobial formulation thus used (comprising at lease one antimicrobial agent) is specific to the microorganism sought.

Indeed, one of the later steps of the method according to the invention consists of the detection of at lease one specific activity of the microorganism sought by fluorescence and, consequently, the aforementioned fluorescence must be limited to the activity sought.

Moreover, the antimicrobial agents can play a role in the modification of membrane integrity for the targeted microorganisms and thus the measurable parameters such as the membrane potential, the oxidation-reduction potential, or dehydrogenase activity. For example, the antimicrobial agents used to select *Listeria* are composed of at least polymixin B, ofloxacin, amphotericin B, 5-fluorocytosine, and lithium chloride. The selective agents for *Salmonella* are composed of brilliant green and sulfapyridine. The selective agents for *Staphylococcus aureus* are comprised of glycine, lithium chloride, and deferoxamine. Selection of *Escherichia coli* is made by bile salts. The selective agents for *Mycobacterium avium paratuberculosis* are comprised of vancomycin hydrochloride and nalidixic acid. The selective antibiotics for *Legionella pneumophila* are comprised of a polymixin B, vancomycin, and cycloheximide mixture.

By "conditioning" the microorganism sought in a sample according to the method of the invention, it is meant "inducing" or "activating" at least one specific activity or property of the aforementioned microorganism. This step is important and is intended to make possible the detection of the specific activity or property in question using a fluorescent label.

For example, the conditioning of the microorganism sought can consist of the induction of an enzymatic activity characteristic of the microorganism sought by adding a non-fluorescent substrate that is specific to the aforementioned enzyme to the microorganism's enrichment medium.

It should be stressed that the conditioning can comprise the induction of one or several enzymatic activities.

The non-fluorescent substrates specific to the enzymes sought are, for example: isopropyl-$\beta$-D-thiogalactopyranoside and melibiose-methyl-$\beta$-D-galactopyranoside to activate $\beta$-D-galactosidase; methyl-$\alpha$-D-galactopyranoside for inducing galactosidase; p-nitrophenyl-$\beta$-D-glucuronide, isopropyl-$\beta$-glucuronide, or methyl-$\beta$-D-glucuronide sodium salt for inducing glucuronidase; methyl-β-D-glucoside, cellobiose, and salicin for inducing β-D-glucosidase; methyl-caprylate for inducing caprylate esterase; 4-nitrophenyl-palmitate and methyl-palmitate for inducing palmitate esterase; and 2-methyl-propionic acid for inducing propionate esterase.

In a preferred embodiment of the present invention and in the case where the conditioning consists of the induction of at lease one specific enzymatic activity of the microorganism sought, steps a) and b) of the method of the invention can be carried out simultaneously. In this way, the sensitivity and rapidity of the analysis will be improved. In this case, the total duration of these two phases carried out simultaneously ranges between 6 h and 48 h, preferably between 12 h and 24 h, and still more preferably between 15 h and 18 h.

In the case where the microorganism sought in a sample is a Gram+ bacteria, the conditioning step can also comprise an induction step of at least one surface antigen characteristic of or specific to the aforementioned microorganism, comprised of adding to the microorganism's enrichment medium a yeast extract in a concentration ranging between 5 and 50 g/L, preferably between 10 and 20 g/L, and still more preferably approximately 10 g/L.

The induction of at least one surface antigen, in the case where the microorganism sought is a Gram+ bacteria, in addition to enzymatic induction, is explained by the fact that it is impossible, using the prior art, to carry out immunomagnetic sorting using an antibody directed against cell membrane antigens or cell wall antigens. Under these classical culturing conditions, Gram+ bacteria synthesize an exopolysaccharide capsule for protection against external threats, which can mask the cell wall and cell membrane antigens thus rendering them inaccessible to antibodies. This is the reason why, in a preferred embodiment of the present invention, the inhibition of the synthesis of this capsule is carried out by adding a yeast extract to the enrichment medium, thus activating expression of cell wall and cell membrane antigens therefore rendered accessible to antibodies.

The step for immunomagnetic concentration of the microorganism sought is carried out from the conditioning medium. Immunomagnetic concentration, by means of an antigen-antibody reaction, consists of concentrating the aforementioned microorganism from the conditioning medium.

The antibody, which is conjugated with a magnetic bead and placed in contact with the microorganism sought, is directed against a specific antigen of the aforementioned microorganism. Next, the microorganism-antibody-bead complexes are separated from the medium and the microorganism is then separated from the rest of the complex.

This immunomagnetic concentration step can be carried out with Dynabeads® brand beads according to the manufacturer's instructions, with the exception that the sample volume is doubled. The reaction can also be carried out with beads covalently linked to antibodies (secondary) directed against rabbit antibodies (primary) (Dynabeads MP-280 sheep anti-rabbit IgG).

By way of example, the protocol used can be the following: a sample volume of 1 to 50 ml, preferably 1 to 5 ml, preferably 2 ml, is placed in contact for 30 min at ambient temperature with 1 to 250 µg, preferably 1 to 50 µg, still more preferably 10 µg of antibody directed against the bacteria sought. A quantity of Dynabeads-brand beads (*Listeria, Salmonella,* etc.) ranging between $1 \times 10^6$ and $250 \times 10^6$, preferably between $10 \times 10^6$ and $20 \times 10^6$ preferably $10 \times 10^6$, previously washed in 0.1% PBS (14190-094, Invitrogen SARL)/BSA (ID-BIO SA), is added and all the components are incubated together for 30 min at ambient temperature under continuous gentle motion. Using a magnetic particle concentrator (MPC-E, Dynal Biotech SA, or any other magnetic sorting device), the beads are recovered on the microtube wall by elimination of the residual liquid. The beads are washed in a volume of PBS and then recovered again using a particle concentrator.

When the immunoconcentration reaction is completed, the beads are recovered in 225 µl of PBS. The bacteria are then detached from the beads. The magnetic concentrator then serves to eliminate the beads and the detachment supernatant containing the concentrated bacteria is recovered in a 5 ml tube for the fluorescent labeling reaction.

The immunoconcentration step, in addition to the fact that it concentrates the bacteria of interest and thus increases detection sensitivity by a factor of 10, makes possible the elimination of bacteria that were able to develop in the enrichment or conditioning medium in spite of the selective elements.

In another embodiment of the invention, the antibody conjugated to the magnetic bead is directed against an antigen specific to the microorganism sought. In other words, a first antigen-antibody reaction is carried out by placing the microorganism sought in contact with an antibody termed "primary" that is directed against an antigen specific to this microorganism and a second antigen-antibody reaction is carried out by placing the "primary" antibody in contact with an antibody termed "secondary" that is conjugated with a magnetic bead and directed against the aforementioned primary antibody.

In a preferred embodiment of the present invention, the diameter of the magnetic beads ranges between 1 and 20 µm, preferably between 2 and 8 µm. Still more preferably, the beads used in the examples have, as indicated, a diameter of 2.8 µm or 4.5 µm The size of the beads used in the present invention is important because it must make it possible to extract bacteria from complex media with great efficiency. In the prior art, beads with much smaller diameters than those described by the invention have been used (nanobeads) but the inventors have shown that these give rise to far too much background noise, which makes it impossible to clearly distinguish the microorganisms from the other elements in the medium The fluorescent labeling of the microorganisms sought, preferably obtained after immunomagnetic concentration, is carried out by adding to the medium containing the aforementioned microorganisms at least one substrate comprising one part specific to the enzymatic activity to be indicated and one label part.

By the choice of these substrates, according to whether they are used by the microorganism or not, it is possible to differentiate and characterize the species or subspecies of a given microbial genera.

In a preferred embodiment of the invention, the label part consists of a fluorogenic label excited at 488 nm chosen from the group comprising the xanthenes, acridines, phycobiliproteins, cyanine, and esculin.

Among the xanthenes, fluorescein and derivatives of fluorescein, for which examples are given below, as well as rhodamine can be cited more particularly. Among the phycobiliproteins, phycoerythrin can be cited quite particularly.

In the case where several substrates are used, each can comprise a label part different than the others, and in this way, for example, several colors of fluorescence can be expressed.

In the context of the present invention, it is important that the transformation of the substrate takes place inside the bacteria and that the fluorescent product is retained in the cell.

Alternatively, transitory permeability if the bacteria can be carried out by adding 15% isopropanol and incubating for 15 min at 37° C.

The choice of fluorescent labels is based on their capacity to be retained inside the cells. For example, carboxylated, aminated, and pentafluorobenzoylaminated forms of fluorescein are particularly well retained in cells, following intracellular enzyme action that fixes these free fluorescence products in the cells (Haugland, 1995).

In another embodiment of the invention, the substrate part specific to the enzymatic activity to be indicated consists of a fatty acid, a monosaccharide, a phosphate, a peptide and/or a sulfate.

Fatty acids are characterized by a carbon chain in the range of 2 to 20 carbon atoms in length. Preferably, the substrate is chosen from the group comprising fluorescein-di-caprylate, fluorescein-di-palmitate, fluorescein-di-dibutyrate, fluorescein-di-dicaproate, fluorescein-di-dilaurate, fluorescein-di-propionate, and 5(6)-carboxy-dichloro-fluorescein-diacetate.

The oses are pentoses or glucuronic acids. Preferably, the substrate is chosen from the group comprising fluorescein-di-β-D-galactopyranoside, fluorescein-α-D-galactopyranoside, fluorescein-di-β-D-glucopyranoside, fluorescein-di-β-D-mannopyranoside, fluorescein-di-β-D-fucopyranoside, fluorescein-di-β-D-N-acetylgalactosaminide, fluorescein-di-β-D-N-acetylglucosaminide, and fluorescein-di-β-D-xyloside.

Preferably, the peptidic substrates are amino acid chains (from 1 to 10 amino acids) conjugated to rhodamine 110.

Preferably, the phosphate and sulfate substrates are fluorescein-diphosphate and fluorescein-disulfate, respectively.

Preferably, the fluorescent substrates that make possible the detection of esterase, osidase, phosphatase, peptidase, or sulfatase activity are added to the conditioning media at a concentration ranging between 0.1 μM and 1 mM, preferably 1 μM to 100 μM.

By way of example, the following substrates are particularly desirable:

5,6-carboxy-dichloro-fluorescein-diacetate to indicate the strong esterase activity of *Listeria monocytogenes* and for the acidic conditions of this bacteria's intracellular contents;

5-(pentafluorobenzoylamino)fluorescein or fluorescein-di-beta-D-glucopyrannoside to indicate the beta-D-glucoside activity of *Listeria monocytogenes*, the aforementioned activity being amplified in *Listeria monocytogenes* by the addition of salicin substrate preferably in the conditioning medium at a concentration of 1 to 10 mM;

fluorescein-dipropionate to indicate the propionate esterase activity of *Listeria monocytogenes*; the induction of this enzyme is carried out by adding 2-methyl-propionic acid preferably in the conditioning medium at a concentration of 1 to 10 mM;

fluorescein di-phosphate as the indicator for alkaline phosphatase activity in *Staphylococcus aureus*; an inhibition of the enzyme in non-aureus *Staphylococcus* can be carried out by adding 0.3% inorganic phosphate to the conditioning medium;

fluorescein-di-beta-D-glucuronic acid or 5-(pentafluorobenzoylamino)fluorescein-di-beta-D-glucuronic acid as the glucuronidase indicator in *Escherichia coli*; in the microorganism, enzyme induction is carried out by adding 1 to 10 mM 4-nitrophenyl-beta-D-glucuronide to the conditioning medium.

fluorescein-di-palmitate or 5-(6)carboxyfluorescein-di-palmitate as the indicator for palmitate esterase in *Mycobacterium avium paratuberculosis*; enzyme induction in the microorganism is carried out by adding 1 to 10 mM 4-nitrophenyl palmitate or methyl-palmitate to the conditioning medium;

fluorescein-di-caprylate or 5-(6)carboxyfluorescein-di-caprylate as the indicator for caprylate esterase in *Salmonella*; enzyme induction in the microorganism is carried out by adding 1 to 10 mM methyl-caprylate to the conditioning medium.

The enzymatic reactions can occur in a temperature range varying between 25° C. and 45° C. depending on the microorganisms, away from light and for a duration not to exceed 1 h. As soon as the labeling reaction is completed, the microorganisms are stored at 4° C. to limit their development and above all to prevent the outflow of label to the microorganism's exterior.

In addition, it should be stressed that when the conditioning step of the method according to the invention consists of an induction step for at least one enzymatic activity specific to the microorganism sought, the immunomagnetic concentration step can be carried out before the conditioning step for the microorganism in question, or after the fluorescent labeling step for the microorganism.

In other words, the conditioning step for the microorganism sought can be carried out in a medium comprising the aforementioned microorganism previously concentrated immunomagnetically. Thus, the fluorescent labeling will take place after the conditioning step; but it is also possible to consider that the fluorescent labeling step for the microorganism can take place immediately after the conditioning step and that the immunomagnetic concentration of the microorganism can take place only after the aforementioned fluorescent labeling.

In a preferred embodiment of the invention, the detection and analysis of the fluorescence making possible the numeration or counting of the microorganisms sought is carried out by a technique chosen from the group comprising: flow cytometry and filtration cytometry with fluorescence microscopy, with flow cytometry being preferred.

Flow cytometry has proved itself particularly desirable, as the final step of the method according to the invention, in order to be able to produce results that are reliable and rapid, which is to say in 24 h, or even in 12 h.

In the field of microbiology, flow cytometry has recently known several developments: counting total microorganisms using non-specific cellular markers and detecting and identifying microorganisms using specific markers (immunoglobulins or genetic markers) coupled to fluorochromes (Robinson J. P., 1999).

Moreover, this technique applies perfectly well to the different types of samples mentioned above but also has application in veterinary diagnostics and environmental analyses.

In an animal contaminated by pathogenic microorganisms, the presence of these pathogens can be indicated using direct or indirect methods. The direct approach consists of detecting the aforementioned microorganisms in biopsies or tissues by culturing in an appropriate medium (Petri dish method), detecting microbial antigens by ELISA techniques, or searching for target DNA sequences. The indirect approach consists of detecting antibodies directed against microbial antigens that are produced in response to the animal's infection by these microorganisms. The goal is to diagnose as early as possible the state of the animal's health, in order to avoid contamination of the other animals. The analysis methods must therefore be rapid and be applied in the early stage of the disease. Thus, it is necessary to improve the detection of bacteria that grow very slowly in a culture medium (mycobacteria for example) or that propagate very quickly in livestock and at times are passed imperceptibly during what is referred to as the asymptomatic phase (paratuberculosis and bovine mucosal disease, for example).

As previously indicated, the samples likely to be analyzed by the method according to the invention can be of diverse origin but also of diverse consistency and/or nature. Thus, the physical characteristics of the aforementioned sample can require a step that is preliminary to steps a), b), c), d), and e) of the method of the invention. More particularly, the preliminary step is a filtration step for the sample being analyzed.

In the case, for example, where the sample to analyze is a solid or semi-solid sample, or a sample comprised of a turbid liquid, the aforementioned filtration, also referred to as particle size reduction, is carried out by means of a filter with a porosity in the range between 20 and 150 microns, preferably between 30 and 100 microns, and still more preferably approximately 63 microns.

By way of example, filtration of solid samples can be carried out in a plastic bag in which is inserted a full-surface plastic filter with the porosity mentioned above.

In the case where the sample to be analyzed by the method according to the invention consists of a clear liquid, it can be filtered through a membrane with a porosity in the range between 0.2 and 10 μm, preferably 0.2 and 5 μm, and still more preferably between 0.2 and 0.5 μm.

The present invention also relates to an enrichment medium selective for a microorganism sought in a sample comprising a nutrient composition making possible the multiplication of the aforementioned microorganism, a composition to revivify the aforementioned microorganism, and possibly a composition to destroy the aforementioned microorganism's competitive flora.

In a preferred embodiment of the invention, the enrichment medium comprises:
  sodium pyruvate at a concentration ranging between 1 and 20 g/L, preferably between 1 and 10 g/L, and more preferably between 4 and 6 g/L,
  sodium thiosulfate at a concentration ranging between 0.5 and 5 g/L, preferably between 0.5 and 3 g/L, and still more preferably approximately 2 g/L,
  catalase at a concentration ranging between 500 and 20 000 u/L, preferably between 2 000 and 8 000 u/L, and still more preferably approximately 5 000 u/L.

The aforementioned enrichment medium for the microorganism sought in the sample to analyze can also comprise at least one antibiotic.

Finally, the present invention also relates to a kit with which to implement the above-described method for detecting and counting microorganisms, this kit comprising:
  an enrichment medium according to the present invention in a liquid or dehydrated form,
  a plastic bag in which is integrated a full-surface filter, preferably made of plastic, with a porosity of approximately 63 μm,
  magnetic beads on which are conjugated antibodies specific to the aforementioned microorganisms, as described above, stored in a liquid medium, for example inside another glass container,
  one or several substrates such as those described above the fluorescent labeling of the aforementioned microorganisms, in a lyophilized form, and
  appropriate solvents, for example in another glass container.

The present description will be best understood in the light of the examples below. These examples specify neither the nature nor the origin of the sample to be analyzed. They identify the microorganism sought and illustrate the detection of this microorganism, it being understood that the protocol described is the same regardless of the nature or origin of the sample. Only the particle reduction or filtration step for the sample, prior to the enrichment step, is not described.

EXAMPLES

Example 1

Detection of *Listeria monocytogenes*

A method for activating the enzyme beta-D-glucosidase and type 1 and type 4 somatic antigens in *Listeria monocytogenes*, and detection by cytometry.

*Listeria monocytogenes* is a Gram positive, catalase-positive, oxidase-negative, non-sporulating, non-encapsulated *bacillus*, pathogenic for man in whom it is responsible for listeriosis, a disease that can cause abortion, septicemia, and meningoencephalitis.

It forms part of the *Listeria* genera that includes six species (*monocytogenes, ivanovii, innocua, welshimeri, seeligeri* and *grayi*). The strains of *Listeria monocytogenes* are divided into 17 serotypes based on the somatic (from 1 to 15) and flagellar (from A to E) antigens of which three (1/2a, 1/2b, and 4b) represent 95% of the isolated strains and are responsible for human listerioses (Swaminathan et al., 1995).

The survival and multiplication characteristics of this bacterium explain its wide distribution. It can multiply in the absence of oxygen, in pH of from 5.6 to 9.6 and at temperatures ranging between 1° C. and 45° C.; it is resistant to salt (up to 20% for certain strains), desiccation, and freezing. Lastly, it can form or participate in biofilms that favor its persistence in spite of cleaning and disinfecting.

Able to persist in conditions that are hostile for most other germs, it is however not very competitive and is inhibited by complex microbial flora. In food matrices, *Listeria monocytogenes* are sometimes in very low numbers and associated with a complex flora often composed of streptococci, enterococci, micrococci, *Bacillus* sp., *Escherichia coli, Pseudomonas aeruginosa*, and *Proteus vulgaris* (Kramer et Jones, 1969).

*Listeria* is mainly transmitted by contaminated food. The infectious dose that causes clinical cases is higher that 100 germs per gram or per milliliter.

The enzyme β-D-glucosidase is present in all *Listeria* species but only the species monocytogenes possesses the phosphatidylinositol phospholipase C (Notermans et al., 1991). Phosphatidylinositol phospholipase C activity is also found in other microbial species such as *Bacillus*.

The characteristics of *Listeria monocytogenes* related to growth, serology, and biochemistry dictate the composition of the enrichment medium used to revivify and multiply *Listeria monocytogenes* from complex samples, while at the same time inhibiting competitive bacteria, in order to stimulate the production of type 1 and type 4 somatic antigens and to induce expression of the enzyme β-D-glucosidase that will serve in the detection of bacteria by the use of a fluorescent substrate.

The selective broth commonly used for *Listeria* is 1/2 Fraser. The composition of this medium served as the base for our broth with regard to the non-selective enrichment base. To this base is added a revivification supplement that makes it possible to correct a deficiency of 1/2 Fraser, which is the ability to reveal stressed bacteria. In addition, a supplement to induce β-D-glucosidase activity is added. The 1/2 Fraser selective supplement was modified to be effective for all the complex products on which the complete *Listeria monocytogenes* detection procedure was conducted.

Another particular procedure for *Listeria monocytogenes* consists in activating the enzyme propionate esterase by adding 2 mM propionic acid to the conditioning medium. This activity is absent in enterococci or other Gram positive cocci that can develop non-specifically in the broth.

1) Compositions a. Non-Selective Enrichment Base.

Tryptone peptone at 5 to 15 g/L, preferred concentration 10 g/L; yeast extract at 5 to 15 g/L, preferred concentration 10 g/L; $Na_2HPO_4$ at 9.6 g/L; $KH_2PO_4$ at 1.35 g/L; NaCl at 10 to 30 g/L, preferred concentration 20 g/L.

Tryptone peptone and yeast extract are sources of nitrogen, carbon, vitamins, and minerals. They make antigen production possible. The salts $Na_2HPO_4$ and $KH_2PO_4$ make it possible to adjust the medium's pH to 7±0.2, which is the optimal growth pH for *Listeria*, and to buffer the medium during enrichment. The purpose of the strong concentration of NaCl is to inhibit enterococci, which are floras frequently associated with *Listeria* and that share common characteristics with it, β-D-glucosidase activity in particular.

b. Revivication Supplement.

Sodium pyruvate at 1 to 10 g/L, preferred concentration 5 g/L; sodium thioglycolate at 0.5 to 5 g/L, preferred concentration 2.5 g/L; and catalase at 5 000 u/L.

Sodium pyruvate and thioglycolate are added to participate in the stimulation of the metabolism of stressed organisms. Catalase acts to eliminate species that are reactive to oxygen, toxic to microorganisms, and possibly present in food.

c. β-D-glucosidase Activity Induction Complement.

Salicin at 1 to 20 mM, preferably 2 mM.

In the same way as some β-D-glucosidases in fungi (Birk et al., 1997; Perez-Pons J. A. 1995; Venturi et al., 2002) or bacteria (Yang et al., 1996), β-D-glucosidase in *Listeria monocytogenes* is inducible. In the absence of inductor during the enrichment stage, enzymatic activity is undetectable.

Salicin is a substrate for β-D-glucosidase; its presence in the enrichment broth makes possible the induction of expression of this enzyme and its detection by flow cytometry (cellobiose or methyl-β-D-glucoside can also be used).

d. Propionate Esterase Induction Activity Complement.

2-methyl-propionic acid at 1 to 20 mM, preferred concentration 2 mM.

The presence of 2-methyl-propionic acid in the conditioning broth makes it possible to induce propionate esterase activity in *Listeria monocytogenes*, for its detection by fluorescent labeling and flow cytometry.

e. Selective Complement.

Polymixin B at 5 mg/L; ofloxacin at 1 mg/L; amphotericin B at 2 mg/L; 5-fluorocytosine at 4 mg/L; and possibly lithium chloride at 9 g/L.

Polymixin B is a bactericidal antibiotic active on Gram-negative bacteria, acting in particular on *Escherichia coli* and *Pseudomonas aeruginosa*. Ofloxacin complements the action of polymixin B on Gram-negative bacteria with a bactericidal activity on *Proteus vulgaris*, among others. In 1/2 Fraser, it is the lithium chloride associated with nalidixic acid that inhibits Gram-negative bacteria; they have no effect on *Pseudomonas* or *Proteus*. Ofloxacin activity is also present in some species of streptococci and staphylococci. Amphotericin B is fungistatic or fungicidal depending on the strain and 5-fluorocytosine is fungicidal. There is no fungicide in the composition of 1/2 Fraser. Some products, in particularly chipolata sausages, are loaded with yeasts that interfere with beta-D-glucosidase reaction and detection. Acriflavin, which inhibits Gram-positive cocci, is not added to the conditioning medium because it causes elements in the medium to fluoresce thus creating background noise on the cytograms, which interferes with their reading. The most troublesome cocci for the procedure are those with β-D-glucosidase activity and it is for these cocci that growth is inhibited by the strong concentration of NaCl in the broth. The elimination of false positives resulting from labeling glucosidase activity in Gram-positive cocci can be accomplished by indicating propionate-esterase activity, which is absent in cocci and inducible in *Listeria monocytogenes*.

The sample is diluted in the broth without selective supplement, by a factor of from 5 to 10 (w/w). The incubation temperature to use is 30° C. and incubation time is 12 h. After 4 hours of revivification, the selective supplement is added, followed by selective enrichment for 8 h at 30° C.

2) Immunoconcentration

The reaction is carried out using magnetic beads (Dynabeads®-*Listeria*, Dynal Biotech, 2.8 μm diameter, for example) following the manufacturer's instructions, although this antibody is not specific to the species *Monocytogenes*.

Various antibodies can be used on the beads:
- a specific antibody "*Listeria* O antiserum poly Serotypes 1,4" (BD Diagnostics Systems, item 223021), which is specific to the strains of *Listeria monocytogenes* responsible for listerioses in humans and which express type 1 and type 4 antigens,
- a serum specific to *Listeria monocytogenes* developed by inoculating a rabbit with inactive bacteria, the aforementioned bacteria having been previously cultured in conditioning broth.

This step can be carried out indirectly with a first reaction in the presence of a primary antibody (one of the two cited above) not conjugated with beads, then immunoconcentration carried out with beads coated with a secondary antibody that recognizes the primary antibody (Dynabeads M-280 sheep anti-rabbit IgG, 2.8 μm diameter, item 112-01, Dynal Biotech, for example).

3) Enzymatic Labeling a. Detection of Esterase Activity.

The substrate 5,6-carboxy-dichloro-fluorescein-diacetate (Fluka Sigma-Aldrich Chemistry SARL, item 21884) is prepared in dimethyl formamide at a concentration of 10 mM, then diluted to 10 μM in PBS. The labeling reaction is accomplished with 25 μl of the dilution added to the supernatant from the immunoconcentration detachment step for 15 min at 37° C. During the reaction, 5(6)-carboxy-dichloro-fluorescein-diacetate is released in the microorganism and becomes fluorescent. A characteristic of this molecule is that it emits green fluorescence when in the acidic pH range (Nedergaard et al., 1990).

This label shows specificity for *Listeria monocytogenes* with respect to a number of other strains when it is used a final concentration of 1 μM (*Salmonella, Staphylococcus aureus, Escherichia coli, Proteus vulgaris, Bacillus* sp., *Yersinia alvei*). Undoubtedly a particular characteristic of this bacteria, this observation is related to the fact that the bacteria possesses higher esterase activity than the other *Listeria* species, a characteristic which doubles in more acidic intracellular pH (personal observations). If salicin is selected for the detection of *Listeria* by flow cytometry, note that it is not used in the enrichment medium.

b. Detection of β-D-glucosidase Activity.

The substrate fluorescein di-β-D-glucopyranoside or pentafluorobenzoylaminofluorescein-di-β-D-glucopyranoside is prepared at 20 mM in water following instructions from Molecular Probes. It is diluted to 4 mM in $H_2O$ before its final use at 500 µM.

In the case where the substrate is fluorescein-di-β-D-glucopyranoside, the bacteria recovered by immunoconcentration are made permeable by the addition of 15 µL of isopropanol followed by a short incubation of 5 min at 37° C. before addition of the substrate.

In all cases, the enzymatic reaction is carried out at 37° C. for 1 h, then immediately placed at 4° C.

c. Detection of Propionate Esterase Activity.

The substrate fluorescein-dipropionate is prepared at a concentration of 10 mM in 10 mM DMSO. It is added to the sample such that the final concentration of the substrate is 100 µM. The sample is thus incubated for 15 min at 37° C., then immediately placed at 4° C. to await analysis.

Example 2

Detection of *Salmonella*

Procedure for activating the enzyme caprylate esterase, the expression of *Salmonella* surface antigens, and detection by cytometry.

Daniel E. Salmon, a veterinarian in the United States, discovered the first strain of *Salmonella* in 1885. To date, 2 213 strains are known and the list continues to grow. *Salmonella* are Gram-negative, facultatively anaerobic (oxidase-negative, catalase-positive, asporous) bacilli that reduce nitrates to nitrites and ferment glucose. The genus *Salmonella* comprises more than 2 500 serotypes of which approximately 50 are truly significant in our region. The antigenic formula is based on the nature of the somatic (O), flagellar (H), or capsular (K/Vi) antigens. This capsular antigen masks the O antigen and is revealed after heating. The O antigens correspond to LPS lipopolysaccharides. Some strains, the R or T forms, can lose all or part of this antigenic ability. Antigen H is subject to a phase variation phenomenon: it can be found in two forms, referred to as 1 and 2.

The primary cause of collective food poisoning, salmonellosis alone represents approximately ⅔ of these cases. In recent years, a spectacular increase, in number and in severity, of human salmonellosis cases has been seen. In comparison with 1980, certain countries have experienced a 20-fold increase in the last 10 to 15 years. A deeper look at the epidemics reveals that the majority of the cases originate from *Salmonella enteritidis* and *Salmonella typhimurium* strains, or more precisely, serotypes. The situation has worsened since the beginning of the 1990's: *S. typhimurium* strains, resistant to a number of antibiotics, have appeared and are likely to become a serious public health problem.

Humans most often contract salmonellosis by consuming contaminated food of animal origin, raw or not thoroughly cooked (primarily meat, poultry, eggs, and milk), although a great number of other foods have been implicated in transmission. The causal agent moves through the food chain from primary production, or because of cross-contamination with foods in the home, or in collective food services or institutions such as hospitals. The bacteria still multiply at 5° C.-12° C., even at temperatures below 5° C. They well tolerate freezing, salt, and desiccation.

Person-to-person transmission is rare in developed countries but occurs nevertheless, particularly in institutions such as neonatal care units or retirement facilities.

Epidemiologically, three groups of *Salmonella* are classified as a function of their adaptation to human or animal hosts and O-somatic antigens:

group B (51.8% of cases), for example *Salmonella typhimurium* and *Salmonella paratyphi* B, cause enteric fever only in humans and higher primates. This group is characterized by strains that systematically express somatic antigen 4 and antigens 1, 5, 12, and 27 depending on the subspecies concerned, group D (19.1% of cases) causes disease in certain animals but rarely in man: *Salmonella dublin* in Bovidae, *Salmonella cholerae-suis* in pigs, and *Salmonella enteritidis* in eggs. However, when such an infection touches humans, it is often invasive and can be fatal. The *Salmonella* comprising this group always express antigen 9 and, depending on the subspecies, antigens 1 and 12, the group C bacteria (20.3% of cases) express antigens 6 and 7, 6 and 8, or 8; those of group E (6.2% of cases) express antigens 3 and 10, 3 and 15, 1 and 3, or 19; those of group G (1.2% of cases) express antigens 13 and 22, or 13 and 23; those of group K express antigen 18; and that of group A, *Salmonella paratyphi* A (0.24% of cases) expresses antigens 1 and 2.

The infectious dose of *Salmonella* is approximately 100 000 germs. The symptoms resulting from an ingestion of such a dose are the typhoid fevers when the implicated serotypes are *Salmonella typhi* and *paratyphi* A, B, and C (House et al., 2001). After an incubation that varies from 1 to 25 days, the disease is triggered with digestive syndromes (diarrhea, abdominal pain, vomiting) before entering into a lymphatic, septicemic phase with fever and torpor. This manifestation is the result of the activity of a neurotropic endotoxin, lipopolysaccharide (LPS), in the cerebrum. Less pathogenic serotypes such as *Salmonella enteritidis, typhimurium, cholera suis, dublin*, etc., are those responsible for less serious food poisonings referred to as salmonellosis.

The pathogenic enterobacteria that constitute part of the *Salmonellae* can be sought directly on selective media that inhibit the growth of Gram-positive bacteria and partially inhibit coliforms, *Proteus*, and other Gram-negatives. Media for this purpose contain bile extract, deoxycholate citrate, sulfate, and brilliant green in various combinations.

The test for β-galactosidase makes it possible to distinguish between strains of *Salmonella* (β-Gal−) and those of *Shigella* (β-Gal+). These two bacterial germs share similar culture conditions and thus are frequently encountered together. A distinctive characteristic of *Salmonella* is its capacity to metabolize caprylic acid (C8 esterase activity). Caprylate esterase activity is measured in a test using 4-methylumbelliferone, which fluoresces when excited by UV light (Humbert et al., 1989; Olsson et al., 1991). Certain culture media use a combination of two chromogenic substrates because the Salmonellae are β-galactosidase negative and glucuronate positive (SM ID culture media).

1) Compositions a. Non-Selective Enrichment Base.

Tryptone peptone at 5 to 15 g/L, preferred concentration 10 g/L; NaCl at 10 to 30 g/L, preferred concentration 20 g/L; yeast extract at 5 to 15 g/L, preferred concentration 10 g/L; D-glucose at 0.5 to 3 g/L, preferred concentration 1 g/L; $Na_2HPO_4$ at 5 to 15 g/L, preferred concentration 9.6 g/L; and $KH_2PO_4$ M at 0.5 to 3 g/L, preferred concentration 1.35 g/L.

Tryptone peptone and yeast extract are sources of nitrogen, carbon, vitamins, and minerals. They make antigen production possible. The salts $Na_2HPO_4$ et $KH_2PO_4$ make it possible to adjust the medium's pH to 7±0.2, which is the optimal growth pH for *Salmonella*, and to buffer the medium during enrichment. The purpose of the strong concentration of NaCl is to inhibit enterococci.

b. Revivication Supplements.

Sodium pyruvate at 1 to 10 g/L, preferred concentration 5 g/L; sodium thioglycolate at 0.5 to 5 g/L, preferred concentration 2.5 g/L; and catalase at 5 000 u/L.

Sodium pyruvate and thioglycolate are added to participate in the stimulation of the metabolism of stressed organisms (Bailey and Cox, 1992). Catalase acts to eliminate species that are reactive to oxygen, toxic to microorganisms, and possibly present in food. Incubation temperature is in the range between 20 and 40° C., preferably 35° C.

c. Caprylate Esterase Activity Induction Complement.

4-nitrophenyl caprylate is a substrate of caprylate esterase; its presence in the enrichment broth makes possible the induction of the expression of this enzyme and its detection by flow cytometry.

d. Selective Complement.

Brilliant green at 1 to 10 mg/L, preferred concentration 5 mg/L, to inhibit the growth of Gram-positive bacteria; and sulfapyridine at 1 g/L to inhibit the development of *E. coli* in particular.

These complements do not generate autofluorescence in contrast to the complements used traditionally (for example sodium taurocholate or other biliary salts, phenol red, ferric citrates) which are responsible for strong autofluorescence in the medium as well as the formation of incrustations (refractive bodies) in the bacteria. In the presence of induction supplement, caprylate esterase activity supplement, and selective supplements, the incubation temperature is from 20 to 40° C. (preferably 35° C.). The incubation period in the presence of these supplements is from 6 to 15 hours as a function of the detection threshold desired.

2) Immunoconcentration

The reaction is carried out using magnetic beads (Dynabeads®-*Salmonella*, 2.8 µm, Dynal Biotech, for example) following the manufacturer's instructions.

Various antibodies are used on the beads:

a commercially available antibody specific to *Salmonella* (BD Diagnostic Systems, item 2302-50, for example) for direct labeling. This antibody, directed against the antigens 1, 4, 5, and 12, makes it possible to detect the group D *Salmonella*, a serum specific to *Salmonella* developed by inoculating a rabbit with inactive bacteria, the aforementioned bacteria having been previously cultured in conditioning broth.

This step can be carried out indirectly with a first reaction in the presence of a primary antibody (one of the two cited above) not conjugated with beads, then immunoconcentration carried out with beads coated with a secondary antibody that recognizes the primary antibody (Dynabeads M-280 sheep anti-rabbit IgG, 2.8 µm diameter, item 112-01, Dynal Biotech, for example).

3) Enzymatic Labeling: Detection of Caprylate Esterase Activity.

The substrate used by preference is fluorescein-dicaprylate. A stock solution is prepared in acetone at a concentration of from 10 to 400 µM. The final concentration used is from 1 to 40 µM, preferably 10 µM. Incubation in the presence of substrate takes place preferably at 37° C. for 30 minutes to 1 hour, then the microorganisms are immediately placed at 4° C.

Example 3

Specific Detection of *Staphylococcus aureus*

Procedure for activating the enzyme phosphatase, the expression of *Staphylococcus aureus* surface antigens, and detection by flow cytometry.

*Staphylococcus aureus* is a member of the family Micrococcaceae. It is an immobile, non-sporulating, Gram-positive cocci, with an average diameter ranging between 0.8 and 1 µm. Its respiratory metabolism is fermentative. It is catalase-positive and for the majority of its strains coagulase-positive. It is responsible for a number of diseases, such as septicemia, conjunctivitis, endocarditis, and osteomyelitis (Sheagren J. N., 1984)

Protein A and the specific components of the *Staphylococcus aureus* cell wall are masked when the strains are grown on an exopolysaccharide induction medium. These polysaccharides form a capsule and are produced by approximately 90% of *Staphylococcus aureus* strains. Eleven capsular serotypes have been described but the majority of strains isolated belong to serotypes 5 and 8 (Arbeit et al., 1984; Sompolinsky et al., 1985).

The expression of *Staphylococcus aureus* serotypes CP5 and CP8 is largely influenced by environmental conditions and bacterial growth conditions. The production of CP5 is inhibited by high levels of yeast extract. Dassy et al., (1991), and Ouyang et al., (1999), showed the same yeast extract inhibiting effect on the production of the CP8 microcapsule.

Antibodies produced against *Staphylococcus aureus* may be capsulary or membranous. For immunological detection of these bacteria, it is necessary to use a mixture of these two types of antibodies (as is done for the Pastorex Staph Plus test, Biorad) or to prevent production of the exopolysaccharide capsule before proceeding with the antigen-antibody recognition reaction. It is this second strategy that we have chosen to develop, with the focus on a revivification composition that inhibits the production of the polysaccharide capsule.

1) Compositions a. Non-Selective Enrichment Base.

Meat peptone: preferred concentration 8 g/L; casein peptone: preferred concentration 2 g/L; yeast extract: preferred concentration 10 g/L; meat extract: preferred concentration 5 g/L. The meat and casein peptones and the yeast and meat extracts are sources of nitrogen, carbon, vitamins, and minerals. The make possible the growth of *Staphylococcus aureus* and the inhibition of capsule formation.

b. Revivication Supplement.

Sodium pyruvate at 1 to 10 g/L, preferred concentration 5 g/L; sodium thioglycolate at 0.5 to 5 g/L, preferred concentration 2.5 g/L; and catalase at 5 000 u/L.

Sodium pyruvate and thioglycolate are added to participate in the stimulation of the metabolism of stressed organisms (Bailey and Cox, 1992). Catalase acts to eliminate species that are reactive to oxygen, toxic to microorganisms, and possibly present in food.

c. Alkaline Phosphatase Activity Inhibition Complement.

0.3% inorganic phosphate.

Phosphatase activity is one of the activities associated with the enterotoxigenic ability of germs and is therefore indicated for *Staphylococcus aureus* detection.

Alkaline phosphatase activity is constitutive in *Staphylococcus aureus* (Soro et al., 1990). However, as it is inhibited by phosphate in some strains of non-*aureus Staphylococcus* (Soro et al., 1990) it is beneficial to add phosphate ions to the medium.

d. Selective Complement.

Glycine at 12 g/L; LiCl at 5 g/L; and deferoxamine at 0.05 g/L.

Lithium chloride is an inhibitor of Gram-negative bacteria. Glycine is an inhibitor of Gram-positive bacteria and stimulated the growth of Staphylococci. Deferoxamine inhibits the growth of *Staphylococcus epidermis*, which is the only *staphylococcus* besides *S. aureus* to possess phosphatase activity.

2) Immunoconcentration

Various antibodies can be used on the beads:
a commercially available serum specific to *Staphylococcus aureus* (item 50-L030, AGROBIO) for directly binding the antibodies with the membrane antigens,
an antibody specific to *Staphylococcus aureus* developed by inoculating a rabbit with inactive bacteria which had been cultured in the conditioning medium.

This step can be carried out indirectly with a first reaction in the presence of a primary antibody (one of the two cited above) not conjugated with beads, then immunoconcentration carried out with beads coated with a secondary antibody that recognizes the primary antibody (Dynabeads M-280 sheep anti-rabbit IgG, 2.8 µm diameter, item 112-01, Dynal Biotech, for example).

3) Enzymatic Labeling.

a. Detection of Alkaline Phosphatase Activity.

The substrate fluorescein-diphosphate (item F-2999, Molecular Probes) makes it possible to detect alkaline phosphatase activity. It is prepared by dissolution in 100 mM pH 8.0 Tris-HCl to a concentration of 10 mM, then dilution to 1 mM in PBS. The labeling reaction is accomplished with 25 µl of the dilution plus 125 µl of PBS added to the supernatant from the immunoconcentration detachment step for 15 min at 37° C. During the reaction, fluorescein is released and becomes fluorescent (excitation/emission 490/514 nm).

This label shows specificity with regard to some species of *Staphylococci* (*aureus* and *epidermis*), to *Micrococcus luteus*, to *Escherichia coli*, and to several species of Streptococci. The combination of broth and immunoconcentration makes it possible to eliminate the strains susceptible to be positive to fluorescent labeling. Deferoxamine inhibits the growth of *Staphylococcus epidermis*.

Example 4

Detection of *Escherichia coli*

Procedure for activating the enzyme glucuronidase, the expression of *Escherichia coli* surface antigens, and detection by cytometry.

Thomas Escherich discovered this bacterium in 1855. A member of the family Enterobacteriaceae, *Escherichia coli* is a bacterial genus in which only a single species is found; but there are more than 1 000 antigenic types. These serotypes are defined according to their O-somatic (171), K-capsular (80), and H-flagellar (56) antigens. Moreover, the K antigens are subdivided into types A, B, and L. Type B is found exclusively in strains associated with infantile diarrheas.

Rather short (2 to 3 µm×0.7 µm), they are found alone, in pairs, or more rarely in a cluster. They can appear in cocci or bacilli form, or in a filamentous form when in older cultures. Their peritrichous mobility is either insignificant or in the case of serotype 0111, for example, nonexistent. It is very easy to culture them as they well tolerate variation in pH (optimal pH is 7.5). The optimal temperature for growth is 37° C. but they grow between 15° C. and 45° C. and will still multiply at 5° C. They resist heat well: incubated at 45° C. they ferment glucose, mannitol, and lactose with a large production of gas. They are resistant to acidity and to freezing. They remain relatively sensitive to antibiotics and as all enterobacteria they reduce nitrates to nitrites. They ferment glucose and lactose and on occasion saccharose and salicin. Most possess lysine decarboxylase activity.

*E. coli* is a common intestinal flora germ of all animals, including humans. It is a commensal of the intestine that represents 80% of aerobic intestinal flora. The germ is found in fecal matter. From there, it spreads in nature via soil and water. Its presence in the environment always signals fecal contamination. Colorimetric tests are designed to identify its presence in water.

*Escherichia coli* is found principally in raw or insufficiently cooked meats (beef, poultry) and in fecal matter of animal and human origin. Meat-grinding operations are often a source of contamination by this germ. Normally, the primary role of *E. coli* is in the suppression of harmful bacteria and the facilitation of the syntheses of numerous vitamins, for only a minority of *E. coli* strains are capable of causing human infection.

*Escherichia coli* are classified in several groups or pathovars according to their pathogenicity. This pathogenicity is usually based on the capacity to adhere to various cellular receptors. *Escherichia coli* belonging to these pathovars are distinguished seriologically by:

O-somatic antigens: there are 180 varieties of which approximately 30 are frequently encountered in pathogenic strains of type I EPEC (O26, O55, O86, O111, O119, O125-O128, O142, etc.), type II EPEC (O18, O44, O112, O114, etc.), EIEC (O28, O29, O124, O136, O143, O152, etc.), ETEC (O6, O8, O15, O20, O25, etc.), and EHEC (O26, O113, O121, O145, O157, etc.), K-capsular antigens of a polysaccharide A or B nature (a dozen significant B types in the EPEC) or of a protein L nature (pili, in particular CFA antigens), H-flagellar antigens, which are important for EHEC of which the most common serotype is O157:H7.

The majority of pathogenic strains are characterized by a particular OxKyHz type serotype.

When *E. coli* is responsible for acute diarrhea, it can be classified according to four pathotypes: enteropathogenic (EPEC), enteroinvasive (EIEC), enterohemorrhagic (EHEC), and enterotoxigenic (ETEC). The strains are characterized by their capacity to produce an enterotoxin whose action on the enterocytes disrupts the absorption functions normally provided by the intestinal mucosa. These microorganisms can be present in certain foods, such as ground meat, and in the water where they indicate fecal contamination.

They can, if they cross the intestinal mucosa (intestinal wall lesions), become pathogenic and can lead to urinary and biliary infections, genital infections called colibacilloses, and very rarely a septicemia. It acts as an opportunistic pathogen.

1) Compositions a. Non-Selective Enrichment Base.

Tryptone peptone at 10 to 30 g/L, preferred concentration 20 g/L; yeast extract at 5 to 15 g/L, preferred concentration 10 g/L; NaCl at 1 to 10 g/L, preferred concentration 5 g/L; D-lactose at 1 to 10 g/L, preferred concentration 5 g/L; $Na_2HPO_4$ at 5 to 15 g/L, preferred concentration 9.6 g/L, $KH_2PO_4$ at 0.5 to 3 g/L, preferred concentration 1.35 g/L.

Tryptone peptone and yeast extract are sources of nitrogen, carbon, vitamins, and minerals. They make antigen production possible. The salts $Na_2HPO_4$ and $KH_2PO_4$ buffer the medium.

b. Revivication Supplements.

Sodium pyruvate at 1 to 10 g/L, preferred concentration 5 g/L; sodium thioglycolate at 0.5 to 5 g/L, preferred concentration 2.5 g/L; and catalase at 5 000 u/L Sodium pyruvate and thioglycolate are added to participate in the stimulation of the metabolism of stressed organisms (Bailey and Cox, 1992). Catalase acts to eliminate species that are reactive to oxygen, toxic to microorganisms, and possibly present in food.

c. Glucuronidase Activity Induction Complement.

4-nitrophenyl-β-D-glucuronide is a substrate for glucuronidase; its presence in the conditioning medium makes possible the induction of this enzyme's expression and its detection by flow cytometry. It is added to the conditioning medium in a concentration varying from 0.5 to 5 mM, preferably 1 mM final.

d. Selective Complement

Biliary salts at 0.5 to 5 g/L, preferably 1.5 g/L.

They are used to inhibit the development of Gram bacteria, particularly sporulant bacteria and fecal streptococci, and to stimulate the growth of *Escherichia coli*. The incubation temperature in the presence of supplements for inducing glucuronidase activity and selective supplements if from 20 to 50° C., preferably 37° C.

The incubation period in the presence of these supplements is from 6 to 15 hours as a function of the detection threshold desired.

2) Immunoconcentration

Various antibodies can be used and conjugated with beads:
- a commercially available antibody specific to *Escherichia coli* for direct labeling,
- an antibody specific to *Escherichia coli* developed by inoculating a rabbit with inactive bacteria, the aforementioned bacteria having been previously grown in the conditioning medium.

This step can be carried out indirectly with a first reaction in the presence of a primary antibody (one of the two cited above) not conjugated with beads, then immunoconcentration carried out with beads coated with a secondary antibody that recognizes the primary antibody (Dynabeads M-280 sheep anti-rabbit IgG, 2.8 μm diameter, item 112-01, Dynal Biotech, for example).

3) Enzymatic Labeling: Detection of Glucuronidase Activity

The substrate used is preferably fluorescein-di-β-D-glucuronic acid, and still more preferably pentafluorobenzoylamino-fluorescein-di-β-D-glucuronic acid. A stock solution is prepared at a concentration of 10 mM in water. A working solution is prepared at 2 mM in $H_2O$. The final concentration used is from 50 to 500 μM, preferably 160 μM.

Incubation in the presence of substrate is carried out preferably at 37° C. for 30 minutes to 1 hour.

In the case where the substrate is fluorescein-di-β-D-glucuronic acid, the bacteria are made permeable temporarily by the addition of 15 μL of isopropanol for 5 min at 37° C.

In all cases, the fluorescent microorganisms are then immediately places at 4° C. before analysis.

Example 5

Detection of *Mycobacterium avium Paratuberculosis*

A procedure for activating the enzyme palmitate esterase, the expression of *Mycobacterium avium paratuberculosis* surface antigens, and detection by flow cytometry.

*Mycobacterium avium paratuberculosis* is an alcohol-resistant Gram-positive bacterium that measures from 0.5 to 1.5 μm. It forms rough white colonies on Herrold's egg yolk culture medium (HEYM). It is a microorganism that develops very slowly: colonies grown on a solid medium are visible after three or four months of culture. The presence of nutrient supplements in the medium do not increase its speed of growth (Cocito et al., 1994).

The mycobacteria are particularly resistant to physical and chemical factors. *M. avium paratuberculosis* is apparently one of the most resistant bacteria in this family, which explains its ability to survive for so long in the environment. Some factors are likely to decrease its survival time in the environment: desiccation, exposure to sunlight, pH higher than 7.0, and iron-poor soil.

*M. avium paratuberculosis* is related phylogenetically to other species belonging to the same family: it shows greater than 99% DNA homology with *M. avium avium*. This strong genetic homology translates, consequently, into a large number of common antigens. This is not a trivial problem when direct immunological tests are used to specifically detect strains of *M. avium paratuberculosis*.

There are three technologies that form the basis for current analytical laboratory techniques for detecting the bacteria *Mycobacterium avium paratuberculosis*: serology, the polymerase chain reaction (PCR) method, and fecal culture.

Serological analysis is an indirect procedure for detecting anti-*Mycobacterium avium paratuberculosis* antibodies; it makes it possible to obtain results in 24 hours but the absence of specific antigens directed against anti-mycobacteria antibodies renders these tests less sensitive than fecal culture (37%).

The PCR technique is a direct, rapid (24 hours), sensitive analysis but does not make it possible to measure or to differentiate dead bacteria from living. This is an important problem when the analysis of food products that have undergone sterilization is desired. Indeed, the problem can persist in products having undergone significant stress from DNA arising from dead bacteria. Thus, a DNA detection method yields false positives in its results.

Fecal culture is a sensitive, reliable, but very long procedure: results are obtained in 3 to 4 months.

The protocol presented below describes an analytical method, using bovine feces, which makes it possible to determine the presence of *Mycobacterium avium paratuberculosis* and its quantification within a short period of time (5 to 7 days).

Additionally, the quantity of pathogenic bacteria present in feces varies widely during the infection cycle; also, a revivification/enrichment step for the bacteria is introduced in order to improve the sensitivity of detection, particularly during the early stages of *Mycobacterium avium paratuberculosis* infection development.

1) Compositions a. Non-Selective Enrichment Base.

Brain heart infusion at 37 g/L; glycerol at 2.7%, asparagine at 2 g/L; Tween 80 at 0.1%; mycobactin J at 2 ml (Synbiotics Corporation, item ACME), and fetal calf serum at 10% (FCS, Invitrogen). This conditioning medium is a preparation that makes it possible on the one hand to revitalize bacteria that are stressed or have reduced metabolic activity and on the other hand to selectively favor the growth of *Mycobacterium avium paratuberculosis* in the medium.

b. Revivication Supplement.

Sodium pyruvate at 1 to 10 g/L, preferred concentration 5 g/L; sodium thioglycolate at 0.5 to 5 g/L, preferred concentration 2.5 g/L; and catalase at 5 000 u/L.

Sodium pyruvate and thioglycolate are added to participate in the stimulation of the metabolism of stressed organisms (Bailey and Cox, 1992). Catalase acts to eliminate species that are reactive to oxygen, toxic to microorganisms, and possibly present in food.

c. Selective Complement.

Nalidixic acid at 50 mg/L; vancomycin at 50 mg/L.

d. Induction Complement.

4-nitrophenyl-palmitate at a concentration of 0.5 to 5 mM, preferred concentration 2 mM.

The enzyme palmitate esterase is inducible in *Mycobacterium avium paratuberculosis*. 4-nitrophenyl-palmitate is a substrate of this enzyme. Its addition to the conditioning broth makes possible the induction of the expression of this enzyme and its detection by flow cytometry.

*Mycobacterium avium paratuberculosis* bacteria present in bovine feces, although they possess significant infectious potential, are not apt in most cases to develop rapidly in an appropriate medium. The cause of their very slow growth is either environmental stress or reduced metabolic activity. The sodium pyruvate used in MCD8 medium possesses revivification properties likely due to action on the Krebs cycle. In addition, it is understood that a medium rich in fatty acids, particularly palmitic acid and oleic acid (Tween 80), favor the development of microorganisms and *Mycobacterium avium paratuberculosis* in particular. Mycobactin J, while acting as a chelator of $Fe^{2+}$ ions, helps provide this essential ion for mycobacterial growth. Finally, *Mycobacterium avium paratuberculosis* development is always accompanied by the release of toxic hydrogen peroxide ($H_2O_2$) molecules. Catalase, present in the medium, makes it possible to eliminate these cellular metabolism products. The two broad-spectrum antibiotics added to the medium make it possible to limit the development of other bacterial strains initially present in the feces. The enrichment phase in the conditioning medium is recommended for a minimum period or 5 days; very good results are obtained after 7 days of incubation.

2) Immunoconcentration

Various antibodies can be used and conjugated with beads:

a commercially available antibody specific to *Mycobacterium avium* for direct labeling (Biodesign International), an antibody specific to *Mycobacterium avium paratuberculosis* developed by inoculating a rabbit with inactive bacteria, the aforementioned bacteria having been previously grown in the conditioning medium.

This step can be carried out indirectly with a first reaction in the presence of a primary antibody (one of the two cited above) not conjugated with beads, then immunoconcentration carried out with beads coated with a secondary antibody that recognizes the primary antibody (Dynabeads M-450 goat anti-mouse IgG, 4.5 μm diameter, Dynal Biotech, for example).

3) Enzymatic Labeling

Following the magnetic immunoconcentration step, *Mycobacterium avium paratuberculosis* is revealed by a fluorochrome specific to its overall enzymatic activity. This labeling makes it possible to indicate the living bacteria, which are potentially infectious and virulent.

a. Detection of Palmitate Esterase Activity.

The substrate used by preference is fluorescein-di-palmitate.

A stock solution is prepared in acetone at a concentration of from 10 to 400 mM. The final concentration used is from 1 to 40 μM, preferably 10 μM. Incubation in the presence of substrate is carried out preferably at 37° C. for 30 minutes to 1 hour. The fluorescent microorganisms are then immediately placed at 4° C. before analysis.

Example 6

Detection of *Legionella pneumophila*

*Legionella* is a non-sporulating, strict aerobic, Gram-negative bacilli measuring from 0.2 to 0.5 μm. With a coccobacillary form in infected tissue, on artificial media it exists in a filamentous form or in grayish polymorphic colonies. The genera *Legionella* currently comprises 43 species and 64 serotypes. Their natural habitat is water and they are currently recognized as intracellular parasites in amoebae. Responsible for pathologies in humans (the legionelloses), *Legionella pneumophila* 1 is the most common pathological serogroup (80% of cases).

The factors that favor the multiplication of *Legionella* are water temperature, the presence of biofilms, the presence of amoebae, and water stagnation.

*Legionella* is particularly characterized by its richness in ramified fatty acids, which is unusual for Gram-negative germs. For its development it requires L-cysteine and ferric pyrophosphate, which are essential growth factors, but is does not hydrolyze sugars and does not grow on blood agar media. Finally, it resists heat treatments and strong acids (100° C. for 10 min; 0.2 M HCL).

On an artificial medium, incubation of *Legionella* is carried out at 36° C. for 10 days, with readings on days 3, 7, and 10; its growth is enhanced by 2.5% $CO_2$.

The identification of *Legionella* can be conducted in two different ways: a direct examination by a latex immunoagglutination test or by immunofluorescence using polyclonal or monoclonal antibodies; or culturing on a selective medium. Direct examination has the advantage of being highly specific, which thus makes it possible to identify the serotype precisely; however, this method is not very sensitive and requires a minimum of 10 000 germs/mL to yield results. Thus, these techniques are used in order to identify species and serogroups following a culture on a selective medium.

Culture on a selective agarose medium has the advantage of being relatively sensitive (minimum detection threshold of 50 CFU/mL), but only a presumption of the presence of *Legionella* is possible. This technique must, by necessity, be completed by direct examination (direct immunofluorescence or latex bead immunoagglutination) or by a molecular biology technique (PCR). Consequently, these two techniques possess the major inconvenience of being long, with 10 days required before obtaining a negative result.

1) Compositions a. Non-Selective Enrichment Base.

Yeast extract at 10 g/L; ACES at 10 g/L; alpha-ketoglutarate at 1 g/L; activated carbon at 4 g/L; pH 6.9±0.2; L-cysteine at 0.4 g/L; ferric pyrophosphate at 0.25 g/L.

b. Revivication Supplement.

Sodium pyruvate at 1 to 10 g/L, preferred concentration 5 g/L; sodium thioglycolate at 0.5 to 5 g/L, preferred concentration 2.5 g/L; and catalase at 5 000 u/L.

c. Selective Complement.

Polymixin B at 5 mg/L; vancomycin hydrochloride at 2 mg/L; and cycloheximide at 16 mg/L.

The *Legionella* conditioning medium formula is based on the components described by Pine et al., (1979); the yeast extract, ACES buffer, glycine, and L-cysteine are classical culture media components that provide the growth factors, mineral salts, and amino acids essential to *Legionella* development; alpha-ketoglutarate is known to be a strong bacterial growth activator.

Finally, during the course of its growth *Legionella pneumophila* produces a large quantity of free radicals, which are incompatible with its development, and thus the activated carbon makes it possible to eliminate these toxic molecules. The incubation period in the conditioning medium is from 24 to 72 hours, preferably 48 hours, at an incubation temperature ranging between 20 and 50° C., preferably approximately 37° C.

2) Immunoconcentration.

Various antibodies can be used and conjugated with beads:
a commercially available antibody specific to *Legionella pneumophila* for direct labeling (Abcam, UK), an antibody specific to *Legionella pneumophila* developed by inoculating a rabbit with inactive bacteria, the aforementioned bacteria having been previously grown in the conditioning medium.

This step can be carried out indirectly with a first reaction in the presence of a primary antibody (one of the two cited above) not conjugated with beads, then immunoconcentration carried out with beads coated with a secondary antibody that recognizes the primary antibody (Dynabeads M-450 goat anti-mouse IgG, 4.5 μm diameter, Dynal Biotech, for example).

3) Enzymatic Labeling 200 mM rhodamine 123

Rhodamine 123 is a membrane potential fluorescent label. A change in membrane potential results in weaker incorporation of this fluorochrome in the cells. The distribution of this probe is 1 unit exterior to the cell, 10 000 in the cytoplasmic compartment. In conjunction with the mode of incorporation (potential-dependant), this cellular specificity assures that the fluorescence emitted reflects overall cell activity.

Rhodamine 123, a component of the conditioning medium, will be incorporated into the microorganisms during *Legionella* multiplication and will make it possible to obtain fluorescent bacteria with the optimal emission wavelength of 633 nm.

In addition, adding broad spectrum antibiotics makes it possible to eliminate possible sample contamination by bacteria often associated with *Legionella*, such as *Staphylococcus aureus* or *Pseudomonas aeruginosa*. These antibiotics, which act by decoupling the membrane potential, induce weak or absent rhodamine 123 labeling.

REFERENCES

Alvarez-Barrientos et al. (2000) Applications Of flow cytometry to clinical microbiology. Clinical Microbiology Reviews. 13: 167-195

Amann (1995) Fluorescently labeled rRNA-targeted oligonucleotide probes in the study of microbial ecology. Mol. Evol. 4: 543-554.

Arbeit et al. (1984) Predominance of two newly described capsular polysaccharide types among clinical isolated of *Staphylococcus aureus*. Diagn. Microbiol. Infect. Dis. 2: 85-91.

Bailey and Cox (1992).

Barer et al. (1999) Bacterial viability and culturability. Advances in Microbial Physiology, 41: 93-137.

Birk et al. (1997) Synthesis of isopropyl-1-thio-beta-D-glucopyranoside (IPTGlc), an inducer of *Aspergillus niger* B1 beta-glucosidase production. Appl Biochem, Biotechnol. 66: 25-30.

Breeuwer et al. (1995) Characterization of uptake and hydrolysis of fluorescein diacetate and carboxyfluorescein diacetate by intracellular esterase in *Saccharomyces cerevisiae*, which results in accumulation of fluorescent product. Appl. Envrion. Microbiol. 61: 1614-1619.

Cocito et al. (1994) Paratuberculosis. Clin. Microbiol. Rev. 7: 328-345.

Dassy et al. (1991) Production of type 5 capsular polysaccharide by *Staphylococcus aureus* grown in a semi-synthetic medium. J. Gen. Microbiol. 137: 1155-1162.

Davey et al. (1996) Flow cytometry and cell sorting of heterogeneous microbial populations: the importance of single-cell analysis. Microbiological Reviews. 60: 641-696.

Dudley (1991) Journal of Clinical Immunoassay 14: 77-82.

Garcia-Armesto et al. (1993) Modern microbiological methods for foods: colony count and direct count methods. A review. Microbiologia SEM. 9: 113.

Grant et al. (1998) Isolation of *Mycobacterium paratuberculosis* from milk by immunomagnetic separation. Applied and Environmental Microbiology. 64: 3153-3158.

Gregori et al. (2001) Resolution of viable and membrane-compromised bacteria in freshwater and marine waters based on analytical flow cytometry and nucleic acid double staining. Applied and Environmental Microbiology. 67: 4662-4670.

Haugland (1995) Detecting enzymatic activity in cell using fluorogenic substrates. Biotechnology and Histochemistry. 70: 243-251.

House et al. (2001) Current Opinion in Infectious Disease. 14: 573-578.

Humbert et al. (1989) Rapid identification of *Salmonella* from poultry meat products by using “Mucap test”. Int. J. Food Microbiology. 8: 79-83.

Iannelli et al. (1998). Simultaneous identification of antibodies to *Brucella abortus* and *Staphylococcus aureus* in milk samples by flow cytometry. Journal of Clinical Microbiology. 36: 802-806.

Kramer et Jones (1969) Media selective for *Listeria monocytogenes*. Journal of Applied Bacteriology. 32: 381-394.

Lopez-Amoros et al. (1995) Flow cytometric assessment of *Escherichia coli* and *Salmonella* starvation-survival in seawater using Rhodamine 123, Propidium iodide and oxonol. Applied and Environmental Microbiology. 61: 2521-2526.

Manafi M. (2000) New developments in chromogenic and fluorogenic culture media. International Journal of Food Microbiology. 60. 205-218.

Mason et al. (1995) Journal of Applied Bacteriology. 78: 309-315.

McClelland et al. (1994) Detection of *Salmonella typhimurium* in dairy products with flow cytometry and monoclonal antibodies. Applied and Environmental Microbiology. 60: 4255-4262.

Moter et al. (2000) Fluorescence in situ hybridization (FISH) for direct visualization of microorganisms. Journal of Microbiological Methods. 41: 85-112.

Nebe-von Caron et al. (1995) Viability assessment of bacteria in mixed populations using flow cytometry. J. Microsc. 179: 55-66.

Nedergaard et al. (1990) Dicarboxy-dichlorofluorescein a new fluorescent probe for measuring acidic intracellular pH. Anal. Biochem. 187: 109-114.

Notermans et al. (1991) Phosphatidylinositol-specific phospholipase C activity as a marker to distinguish between pathogenic and non-pathogenic *Listeria* species. Applied and Environmental Microbiology. 57: 2666-2670.

Olsson et al. (1991). Identification of Salmonellae with the 4-methylumbelliferyl caprilate fluorescence test. J. Clin. Microbiol. Vol 29, p 2631.

Ouyang et al. (1999) Promoter analysis of the cap8 operon, involved in type 8 capsular polysaccharide production in *Staphylococcus aureus*. J. Bacteriol. 181: 1155-1162.

Perez-Pons et al. (1995) Induction and preliminary characterization of intracellular beta-glucosidases from a cellulolytic *Streptomyces* strain. FEMS Microbiological Letters. 128: 235-239.

Pinder et al. (1994) Rapid immunoassay for pathogenic *Salmonella* organisms by immunofluorescence flow cytometry. Journal of Microscopy. 176: 17-22.

Robinson J. P. (1999) Overview of flow cytometry. In Current Protocols in Cytometry 11.1.1-11.1.4.

Salzman et al. (1982) Rapid identification of microorganisms by circular-intensity differential scattering. Appl. Env. Microbiol. 44: 1081-1085.

Seo et al. (1998) Immunomagnetic separation and flow cytometry for rapid detection of *Escherichia coli* O157: H7. J. Food Protect. 61:812-816.

Sheagren J. N. (1984) *Staphylococcus aureus*. The persistent pathogen. N. Engl. J. Med. 310: 1368-1373 et 1437-1442.

Skjerve et al. (1991). Immunomagnetic separation of *Salmonella* from foods. International Journal of Microbiology. 14: 11-18.

Skjerve et al. (1990) Detection of *Listeria monocytogenes* in foods by immunomagnetic separation. Applied and Environmental Microbiology. 56: 3478-3481.

Sompolinsky et al. (1985) J. Clin Microbiol. 22: 828-834.

Soro et al. (1990) J. Clin. Microbiol. 28: 2707-2710.

Steen (1986) Simultaneous separate detection of flow angle and large angle light scaterring in an arc lamp-based flow cytometer. Cytometry. 7: 445-449.

Swaminathan et al. (1995) in Muray et al. Eds Manuel of Clinical Microbiology. American Society of Microbiology. Washington D.C.

Tomayasu et al. (1998) Improvement of the immunomagnetic separation method selective for *Escherichia coli* O157 strains. Applied and Environmental Microbiology. 64: 376-382.

Tortorello et al. (1994) Antibody-direct epifluorescent filter technique for rapid direct enumeration of *Escherichia coli* O157: H7 in beef. Applied and Environmental Microbiology. 60: 3553-3559.

Tortorello et al. (1998) Quantitative analysis and isolation of *Escherichia coli* O157: H7 in a food matrix using flow cytometry and cell sorting. FEMS Immunology in Medical Microbiology. 19: 267-274.

Venturi et al. (2002) Extracellular beta-D-glucosidase from *Chaetomium thermophilum* var. *coprophilum*: production, purification and some biochemical properties. Journal of Basic Microbiology. 42: 55-66.

Vlieger et al. (1992) Quantitation of polymerase chain reaction products by hybridization-based assays with fluorescent, calorimetric, or chemiluminescent detection. Analytical biochemistry 205: 1-7.

Wallner et al. (1995) Flow cytometric analysis of activated sludge with rRNA-targeted probes. Appl. Environ. Microbiol. 61: 1859-1866.

Yang et al. (1996) Biol. Pharma Bull. 19: 701-704.

The invention claimed is:

1. A method for detecting and counting individual intracellularly labeled microorganisms in a food, environment or animal-derived sample, wherein background fluorescence is avoided and wherein detection thresholds are on the order of from 10 to 100 microorganisms per gram of sample, comprising the steps of:
   a) selectively enriching the microorganism sought in the sample, so as to revive the microorganism being sought while destroying microorganisms that are not being sought,
   b) inducing or activating at least one enzymatic activity specific to the microorganism being sought,
   c) immunomagnetically concentrating the microorganism,
   d) fluorescently labeling the microorganism by adding to the sample containing the microorganisms at least one substrate comprising one part specific to the enzymatic activity to be indicated and one fluorogenic label, wherein the transformation of the substrate takes place inside the microorganism and wherein the fluorescent product resulting from the fluorogenic label is retained in the microorganism thereby avoiding the production of background fluorescence and permitting the counting of each individual microorganism, and
   e) detecting and counting each fluorescently labeled microorganism by flow cytometry wherein in the method, step a) occurs before step c) and wherein the immunomagnetic concentration of step c) comprises the steps of:
   i) placing the microorganism sought, present in the sample, in contact with an antibody directed against an antigen specific to the microorganism, the antibody being conjugated with a magnetic bead, wherein the magnetic bead has a diameter that is between 1 and 20 µm,
   ii) separating the bead-antibody-microorganism complexes from the sample, and
   iii) separating the microorganism from the rest of the complex.

2. The method according to claim 1, wherein the enrichment step is carried out in a composition comprising:
   sodium pyruvate at a concentration of between 1 and 20 g/L,
   sodium thio sulfate at a concentration of between 0.5 and 5 g/L,
   catalase at a concentration of between 500 and 20,000 IU/L.

3. The method according to claim 2, wherein said composition comprises in addition at least one antibiotic.

4. The method according to claim 1, wherein step b) is an induction step for at least one enzymatic activity specific to the microorganism sought, comprising adding to the microorganism's enrichment medium at least one non-fluorescent substrate specific to said enzyme or enzymes.

5. The method according to claim 4, wherein steps a) and b) are carried out simultaneously.

6. The method according to claim 4, wherein in step c), immunomagnetically concentrating the microorganism takes place before inducing or activating at least one enzymatic activity of the microorganism in step b), or wherein in step c), immunomagnetically concentrating the microorganism takes place after fluorescently labeling the microorganism in step d).

7. The method according to claim 1, wherein in the case where the microorganism sought is a Gram-positive bacteria, step b) comprises in addition to an induction step, further comprises adding to the microorganism's enrichment, medium yeast extract at a concentration of between 5 and 50 g/L.

8. The method according to claim 1, wherein in step c), the antibody conjugated with a magnetic bead is directed against an antibody that is itself directed against an antigen specific to the microorganism sought.

9. The method according to claim 1, wherein the label is a fluorogenic label excited at 488 nm selected from the group consisting of the xanthenes, acridines, phycobiliproteins, cyanine, and esculin.

10. The method according to claim 4, wherein the substrate part specific to the enzymatic activity to be revealed is selected from the group consisting of a fatty acid, a monosaccharide, a phosphate, and a sulfate.

11. The method according to claim 1, wherein steps a), b), c), d), and e) are preceded by a filtration step for the sample to be analyzed.

12. The method according to claim 11, wherein the filtration is carried out by means of a filter whose porosity size is between 20 and 150 microns.

13. The method according to claim 11, wherein the filtration is carried out on a membrane presenting a porosity size of between 0.2 and 10 µm.

14. A method for detecting and counting individual intracellularly labeled microorganisms in a food, environment or animal-derived sample, wherein background fluorescence is avoided and wherein detection thresholds are on the order of from 10 to 100 microorganisms per gram of sample, comprising the steps of:
   a) selectively enriching the microorganism sought in the sample, so as to revive the microorganism being sought while destroying microorganisms that are not being sought,
   b) inducing or activating at least one enzymatic activity specific to the microorganism being sought,
   c) immunomagnetically concentrating the microorganism,
   d) fluorescently labeling the microorganism by adding to the sample containing microorganisms at least one substrate comprising one part specific to the enzymatic activity to be indicated and one part fluorogenic label, wherein the transformation of the substrate takes place inside the microorganism and wherein the fluorescent product resulting from the fluorogenic label is retained in the microorganism, thereby avoiding the production of background fluorescence and permitting the counting of each individual microorganism and
   e) detecting and counting each fluorescently labeled microorganism by flow cytometry;
wherein the microorganisms are enriched in a composition comprising sodium pyruvate, sodium thiosulfate, and catalase; wherein in the method, step a) occurs before step c) and wherein the immunomagnetic concentration of step c) comprises the steps of:
   i) placing the microorganism sought, present in the sample, in contact with an antibody directed against an antigen specific to the microorganism, the antibody being conjugated with a magnetic bead, wherein the magnetic bead has a diameter that is between 1 and 20 µm,
   ii) separating the bead-antibody-microorganism complexes from the sample, and
   iii) separating the microorganism from the rest of the complex.

15. The method of claim 14, wherein the microorganisms are enriched in a composition comprising:
   sodium pyruvate at a concentration of between 1 and 20 g/L,
   sodium thio sulfate at a concentration of between 0.5 and 5 g/L, and
   catalase at a concentration of between 500 and 20,000 IU/L.

16. The method according to claim 1, wherein in step (c) i), the magnetic bead has a diameter that is between 2 and 8 µm.

* * * * *